United States Patent
Fischer et al.

(10) Patent No.: US 6,200,932 B1
(45) Date of Patent: Mar. 13, 2001

(54) PHENYL-SUBSTITUTED CYCLIC KETOENOL

(75) Inventors: Reiner Fischer, Monheim; Udo Schneider, Leverkusen; Peter Dahmen, Neuss, all of (DE); Markus Dollinger, Overland Park, KS (US); Christoph Erdelen, Leichlingen; Ulrike Wachendorff-Neumann, Neuwied, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/230,750

(22) PCT Filed: Aug. 5, 1997

(86) PCT No.: PCT/EP97/04246

§ 371 Date: Feb. 1, 1999

§ 102(e) Date: Feb. 1, 1999

(87) PCT Pub. No.: WO98/06721

PCT Pub. Date: Feb. 19, 1998

(30) Foreign Application Priority Data

Aug. 9, 1996 (DE) ............................................. 196 32 126

(51) Int. Cl.[7] ........................ A01N 43/90; C07D 491/10; C07D 491/20; C07D 493/10; C07D 319/06
(52) U.S. Cl. ...................... 504/225; 504/283; 514/237.2; 514/409; 544/141; 548/410; 549/333; 549/334; 549/371
(58) Field of Search .................. 514/409, 237.2; 548/410; 504/283, 225; 544/141; 549/333, 334, 371

(56) References Cited

U.S. PATENT DOCUMENTS

| | | | |
|---|---|---|---|
| 5,258,527 | 11/1993 | Krauskopf et al. | 548/543 |
| 5,462,913 | 10/1995 | Fischer et al. | 504/138 |
| 5,567,671 | 10/1996 | Fischer et al. | 504/283 |
| 5,589,469 | 12/1996 | Fischer et al. | 514/91 |
| 5,616,536 | 4/1997 | Fischer et al. | 504/225 |
| 5,677,449 | 10/1997 | Fischer et al. | 544/165 |
| 5,981,567 | * 11/1999 | Fischer et al. | 548/410 X |

FOREIGN PATENT DOCUMENTS

95/00020   1/1995 (WO) .
95/20572   8/1995 (WO) .

OTHER PUBLICATIONS

Chem. Reviews, 52, (month unavailable) 1953, pp. 237 to 416, Norman O.V. Sonntag, The Reactions of Aliphatic Acid Chlorides.

Indian J. Chem. 6, Bhattacharya, (month unavailable) 1968, pp. 341–345, Isoquinoline Derivatives: Part XVIII—Formation of I–Alkyl–(or alkaryl or aryl)–3methyl–7–chloro–(or 5–chloro)–isoquinolines.

H. Piotrowska et al, Bulletin De L'Academie Polonaise des Sciences, vol. XIX, No. 10, (month unavailable) 1971, pp. 591–594, Heterocyclic Derivatives of Ethyl Nitroacetate.

J. Org. Chem., 51 (month unavailable) 1986, Polniaszek et al, pp. 3023–3027, Preparation of Potential Intermediates for the Synthesis of Yohimbine and Reserpine.

Tetrahedron, vol. 34, pp. 1651–1660, Omura and Swern, Oxidation of Alcohols by "Activated" Dimethyl Sulfoxide. A Preparative, Steric and Mechanistic Study.

J. Am. Chem. Soc., vol. 63, Oct. 1941, pp. 2635–2636, Some Nitro and Amino Acetals Derived from Polyhydric Nitro Alcohols.

Synthesis, Aug. 1993, pp. 815–818, Schmidt et al, The Total Synthesis of Antrimycin $D_v$; III:[1] Construction of the Protected Hexapeptide and Deproctection.

* cited by examiner

*Primary Examiner*—Fiona T. Powers
(74) *Attorney, Agent, or Firm*—Joseph C. Gil

(57) ABSTRACT

The invention relates to novel phenyl-substituted cyclic ketoenols of the formula (I)

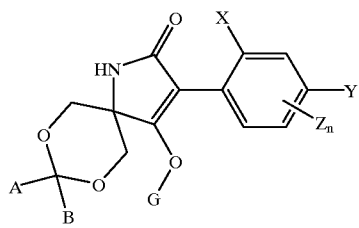

(I)

in which

A, B, G, X, Y, Z and n are each as defined in the description, to a plurality of processes for their preparation and to their use as pesticides and herbicides.

15 Claims, No Drawings

PHENYL-SUBSTITUTED CYCLIC KETOENOL

TECHNICAL FIELD OF THE INVENTION

The invention relates to novel phenyl-substituted cyclic ketoenols, to a plurality of processes for their preparation and to their use as pesticides and herbicides.

BACKGROUND OF THE INVENTION 1H-arylpyrrolidine-dione derivatives (EP-456 063, EP-521 334, EP-596 298, EP-613 884, EP-613 885, WO 94/01 997, WO 95/01358, WO 95/26954, WO 96/00382, WO 95/20572, EP 668 267) having herbicidal, acaricidal and insecticidal action are known.

However, the activity and the activity spectrum of these compounds is, in particular at low application rates and concentrations, not always entirely satisfactory. Furthermore, the crop safety of these compounds is not always sufficient.

DETAILED DESCRIPTION OF THE INVENTION

This invention, accordingly, provides novel compounds of the formula

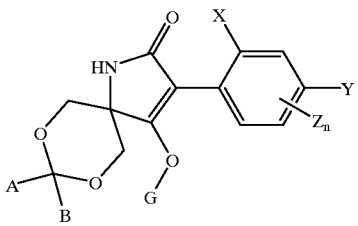

(I)

in which
X represents halogen, alkyl, alkenyl, alkinyl, alkoxy, alkenyloxy, alkylthio, alkylsulphinyl, alkylsulphonyl, halogenoalkyl, halogenoalkenyl, halogenoalkoxy, halogenoalkenyloxy, nitro, cyano or represents phenyl, phenoxy, phenylthio, benzyloxy or benzylthio, each of which is optionally substituted,
Y represents hydrogen, halogen alkyl, alkenyl, alkinyl, alkoxy, alkenyloxy, alkylthio, alkylsulphinyl, alkylsulphonyl, halogenoalkyl, halogenoalkenyl, halogenoalkoxy, halogenoalkenyloxy, nitro or cyano,
Z represents halogen, alkyl, alkenyl, alkinyl, halogenoalkyl, halogenoalkenyl, alkoxy, alkenyloxy, halogenoalkoxy, halogenoalkenyloxy, nitro or cyano,
n represents 0, 1, 2 or 3,
A represents hydrogen, represents alkyl, alkenyl, alkinyl, alkoxyalkyl, polyalkoxyalkyl or alkylthioalkyl, each of which is optionally substituted by halogen, represents saturated or unsaturated cycloalkyl which is optionally substituted and in which optionally at least one ring atom is replaced by a heteroatom, or represents aryl, arylalkyl or hetaryl, each of which is optionally substituted by halogen, alkyl, halogenoalkyl, alkoxy, halogenoalkoxy, cyano or nitro and which may optionally be substituted by substituted phenoxy, benzyloxy or hetaryloxy,
B represents hydrogen or represents alkyl or alkoxyalkyl, each of which is optionally substituted by halogen, or
A and B together with the linking carbon atom represent a saturated or unsaturated, unsubstituted or substituted ring which optionally contains a heteroatom,
G represents hydrogen (a) or represents one of the groups

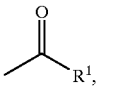

(b)

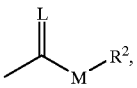

(c)

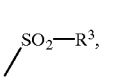

(d)

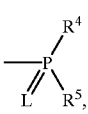

(e)

E or

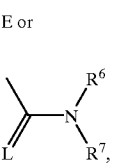

(f)

(g)

in which
E represents a metal ion equivalent or an ammonium ion,
L represents oxygen or sulphur,
M represents oxygen or sulphur,
$R^1$ represents alkyl, alkenyl, alkoxyalkyl, alkylthioalkyl or polyalkoxyalkyl, each of which is optionally substituted by halogen, or represents optionally halogen-, alkyl- or alkoxy-substituted cycloalkyl which may be interrupted by at least one heteroatom or represents phenyl, phenylalkyl, hetaryl, phenoxyalkyl or hetaryloxyalkyl, each of which is optionally substituted,
$R^2$ represents alkyl, alkenyl, alkoxyalkyl or polyalkoxyalkyl, each of which is optionally substituted by halogen, or represents cycloalkyl, phenyl or benzyl, each of which is optionally substituted,
$R^3$, $R^4$ and $R^5$ independently of one another each represent alkyl, alkoxy, alkylamino, dialkylamino, alkylthio, alkenylthio or cycloalkylthio, each of which is optionally substituted by halogen, or represent phenyl, benzyl, phenoxy or phenylthio, each of which is optionally substituted, and
$R^6$ and $R^7$ independently of one another each represent hydrogen, represent alkyl, cycloalkyl, alkenyl, alkoxy or alkoxyalkyl, each of which is optionally substituted by halogen, represent optionally substituted phenyl, represent optionally substituted benzyl, or together with the linking N atom represent an optionally by oxygen- or sulphur-containing ring.

Depending, inter alia, on the nature of the substituents, the compounds of the formula (I) can be present as geometric and/or optical isomers or isomer mixtures of different -composition which can be separated in a customary manner. Both the pure isomers and the isomer mixtures, their preparation and use, and compositions comprising them form part of the subject matter of the present invention. In the following, for simplicity, however, compounds of the formula (I) are always referred to, although both pure compounds and, if appropriate, mixtures having different proportions of isomeric compounds are intended.

Furthermore, it has been found that the novel compounds of the formula (I) are obtained by one of the processes described below:

(A) Substituted 3-phenylpyrrolidine-2,4-diones or enols thereof of the formula (I-a)

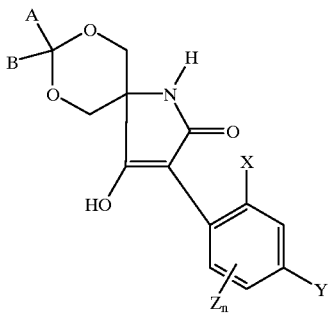 (I-a)

in which
A, B, X, Y, Z and n are each as defined above
are obtained when
N-acylamino acid esters of the formula (II)

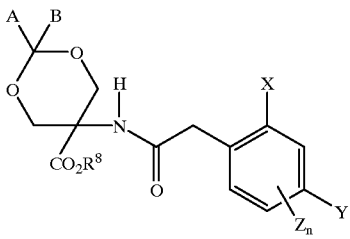 (II)

in which
A, B, X, Y, Z and n are each as defined above and
$R^8$ represents alkyl (preferably $C_1$–$C_6$-alkyl)
are condensed intramolecularly in the presence of a diluent and in the presence of a base.

Furthermore, it has been found (B)α) that compounds of the formula (I-b) shown above in which A, B, X, Y, Z, $R^1$ and n are each as defined above are obtained when compounds of the formula (I-a) in which A, B, X, Y, Z and n are each as defined above are reacted with acyl halides of the formula (III)

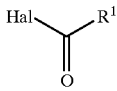 (III)

in which
$R^1$ is as defined above and
Hal represents halogen (in particular chlorine or bromine)
or are reacted
β) with carboxylic anhydrides of the formula (IV)

 (IV)

in which
$R^1$ is as defined above
if appropriate in the presence of a diluent and if appropriate in the presence of an acid binder;

(C) that the compounds of the formulae (I-c) shown above in which A, B, $R^2$, M, X, Y, Z and n are each as defined above and L represents oxygen are obtained when compounds of the formula (I-a) shown above in which A, B, X, Y, Z and n are each as defined above are in each case reacted with chloroformic esters or chloroformic thiol esters of the formula (V)

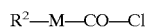 (V)

in which
$R^2$ and M are each as defined above,
if appropriate in the presence of a diluent and if appropriate in the presence of an acid binder;

(D) that compounds of the formulae (I-c) shown above in which A, B, $R^2$, M, X, Y, Z and n are each as defined above and L represents sulphur are obtained when compounds of the formula (I-a) shown above in which A, B, X, Y, Z and n are each as defined above are in each case reacted with chloromonothioformic esters or chlorodithioformic esters of the formula (VI)

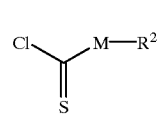 (VI)

in which
M and $R^2$ are each as defined above,
if appropriate in the presence of a diluent and if appropriate in the presence of an acid binder, (E) that compounds of the formula (I-d) shown above in which A, B, $R^3$, X, Y, Z and n are each as defined above are obtained when compounds of the formulae (I-a) shown above in which A, B, X, Y, Z and n are each as defined above are in each case
reacted with sulphonyl chlorides of the formula (VII)

 (VII)

in which
$R^3$ is as defined above,
if appropriate in the presence of a diluent and if appropriate in the presence of an acid binder, (F) that compounds of the formulae (I-e) shown above in which A, B, L, $R^4$, $R^5$, X, Y, Z and n are each as defined above are obtained when compounds of the formulae (I-a) shown above in which A, B, X, Y, Z and n are each as defined above are in each case
reacted with phosphorus compounds of the formula (VIII)

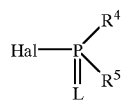 (VIII)

in which
L, $R^4$ and $R^5$ are each as defined above and
Hal represents halogen (in particular chlorine or bromine), if appropriate in the presence of a diluent and if appropriate in the presence of an acid binder, (G) that compounds of the formulae (I-f) shown above in which A, B, E, X, Y, Z and n are each as defined above are obtained when compounds of the formulae (I-a) in which A, B, X, Y, Z and n are each as defined above are in each case reacted with metal compounds or amines of the formulae (IX) or (X)

$$Me(OR^{10})_t \qquad (IX)$$

$$R^{10}\diagdown \underset{\underset{R^{12}}{|}}{N}\diagup R^{11} \qquad (X)$$

in which

Me represents a mono- or divalent metal (preferably an alkali metal or alkaline earth metal such as lithium, sodium, potassium, magnesium or calcium), t represents the number 1 or 2 and $R^{10}, R^{11}, R^{12}$ independently of one another each represent hydrogen or alkyl (preferably $C_1$–$C_8$-alkyl), if appropriate in the presence of a diluent, (H) that compounds of the formulae (I-g) shown above in which A, B, L, $R^6$, $R^7$, X, Y, Z and n are each as defined above are obtained when compounds of the formulae (I-a) shown above in which A, B, X, Y, Z and n are each as defined above are reacted with carbamoyl chlorides or thiocarbamoyl chlorides of the formula (XI), $$R^6\diagdown \underset{R^7\diagup}{N}-\overset{\overset{L}{\|}}{C}-Cl \qquad (XI)$$

in which

L, $R^6$ and $R^7$ are each as defined above, if appropriate in the presence of a diluent and if appropriate in the presence of an acid binder.

Thus, the compounds of the formulae (I-a) according to the invention are important intermediates for preparing the compounds of the formulae (I) according to the invention in which G represents one of the groups b), c), d), e), f) or g).

Furthermore, it has been found that the novel compounds of the formula (I) have very good activity as pesticides, preferably as insecticides, acaricides and herbicides.

The formula (I) provides a general definition of the compounds according to the invention. Preferred substituents or ranges of the radicals listed in the formulae mentioned hereinabove and hereinbelow are illustrated below:

X preferably represents halogen, $C_1$–$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro, cyano or represents phenyl, phenoxy, phenylthio, benzyloxy or benzylthio, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

Y preferably represents hydrogen, halogen, C-$C_6$-alkyl, $C_2$–$C_6$-alkenyl, $C_2$–$C_6$-alkinyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro or cyano, Z preferably represents halogen, $C_1$–$C_6$-alkyl, $C_2$–$C_6$-alkenyl, $C_2$–$C_6$-alkinyl, $C_1$–$C_6$-halogenoalkyl, $C_2$–$C_6$-halogenoalkenyl, $C_1$–$C_6$-alkoxy, $C_3$–$C_6$-alkenyloxy, $C_1$–$C_6$-halogenoalkoxy, $C_3$–$C_6$-halogenoalkenyloxy, nitro or cyano, n preferably represents 0, 1, 2 or 3, A preferably represents hydrogen or represents $C_1$–$C_{12}$-alkyl, $C_2$–$C_8$-alkenyl, $C_2$–$C_8$-alkinyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, each of which is optionally substituted by halogen, represents optionally halogen-, $C_1$–$C_6$-alkyl- or $C_1$–$C_6$-alkoxy-substituted $C_3$–$C_8$-cycloalkyl in which optionally one methylene group is replaced by oxygen or sulphur or represents phenyl or naphthyl, hetaryl having 5 to 6 ring atoms, preferably furanyl, pyridyl, imidazolyl, triazolyl, pyrazolyl, pyrimidyl, thiazolyl or thienyl or phenyl- or naphthyl-$C_1$–$C_6$-alkyl, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro and which may additionally be substituted by optionally halogen-, $C_1$–$C_4$-alkyl-, $C_1$–$C_4$-alkoxy-, $C_1$–$C_2$-halogenoalkyl-, $C_1$–$C_2$-halogenoalkoxy-, cyano- or nitro-substituted phenoxy, B preferably represents hydrogen or represents $C_1$–$C_{12}$-alkyl or $C_1$–$C_8$-alkoxy-$C_1$–$C_6$-alkyl, each of which is optionally substituted by halogen, or A, B and the linking carbon atom preferably represent saturated or unsaturated $C_3$–$C_{10}$-cycloalkyl (in particular $C_5$–$C_8$-cycloalkyl), in which optionally one methylene group is replaced by oxygen or sulphur and which is optionally mono- or polysubstituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the linking carbon atom preferably represent $C_5$–$C_8$-cycloalkyl or $C_5$–$C_8$-cycloalkenyl, in which two substituents together with the linking carbon atoms represent $C_5$–$C_6$-alkanediyl, $C_5$–$C_6$-alkenediyl or $C_6$-alkanedienediyl, each of which is optionally substituted by $C_1$–$C_6$-alkyl, $C_1$–$C_6$-alkoxy or halogen and in which optionally one methylene group is replaced by oxygen or sulphur.

G preferably represents hydrogen (a) or represents one of the groups (b)

$$\underset{}{\overset{\overset{O}{\|}}{\diagup\!\!\!\diagdown}}R^1,$$

(c)

$$\underset{}{\overset{\overset{L}{\|}}{\diagup\!\!\!\diagdown}}M^{R^2},$$

(d)

$$\diagup^{SO_2-R^3}$$

-continued

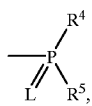
(e)

E or (f)

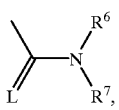
(g)

in which
E represents a metal ion equivalent or an ammonium ion,
L represents oxygen or sulphur and
M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is optionally substituted by halogen, or represents optionally halogen-, $C_1$–$C_6$-alkyl- or $C_1$–$C_6$-alkoxy-substituted $C_3$–$C_8$-cycloalkyl, in which optionally at least one methylene group is replaced by oxygen or sulphur,
preferably represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl,
preferably represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl,
preferably represents optionally halogen- or $C_1$–$C_6$-alkyl-substituted 5- or 6-membered hetaryl (in particular pyrazolyl, thiazolyl, pyridyl, pyrimidyl, furanyl or thienyl),
preferably represents optionally halogen- or $C_1$–$C_6$-alkyl-substituted phenoxy-$C_1$–$C_6$-alkyl or
preferably represents optionally halogen-, amino- or $C_1$–$C_6$-alkyl-susbstituted 5-or 6-membered hetaryloxy-$C_1$–$C_6$-alkyl (in particular pyridyloxy-$C_1$–$C_6$-alkyl, pyrimidyloxy- $C_1$–$C_6$-alkyl or thiazolyloxy-$C_1$–$C_6$-alkyl).

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen,
preferably represents optionally halogen-, $C_1$–$C_6$-alkyl- or $C_1$–$C_6$-alkoxy-substituted $C_3$–$C_8$-cycloalkyl or
preferably represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy.

$R^3$ preferably represents optionally halogen-substituted $C_1$–$C_8$-alkyl or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ and $R^5$ independently of one another each preferably represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$- alkenylthio or $C_3$–$C_7$-cycloalkylthio, each of which is optionally substituted by halogen, or represent phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another each preferably represent hydrogen, represent $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, each of which is optionally substituted by halogen, represent optionally halogen-, $C_1$–$C_8$-halogenoalkyl-, $C_1$–$C_8$-alkyl- or $C_1$–$C_8$-alkoxy-substituted phenyl, optionally halogen-, $C_1$–$C_8$-alkyl-, $C_1$–$C_8$-halogenoalkyl- or $C_1$–$C_8$-alkoxy-substituted benzyl or together represent a $C_3$–$C_6$-alkylene radical in which optionally one methylene group is replaced by oxygen or sulphur.

X particularly preferably represents fluorine, chlorine, bromine, $C_1$–$C_4$-alkyl, $C_1$–$C_4$-alkoxy, $C_1$–$C_4$-halogenoalkyl, $C_1$–$C_4$-halogenoalkoxy, nitro, cyano or represents phenyl or benzyloxy, each of which is optionally substituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano.

Y particularly preferably represents hydrogen, fluorine, chlorine, bromine, $C_1$–$C_4$-alkyl, $C_1$–$C_4$-alkoxy, $C_3$–$C_4$-alkenyloxy, $C_1$–$C_4$-halogenoalkyl, $C_1$–$C_4$-halogenoalkoxy, nitro or cyano.

Z particularly preferably represents fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, nitro or cyano.

n particularly preferably represents 0, 1, 2 or 3 (in particular represents 0, 1 or 2).

A particularly preferably represents hydrogen or represents $C_1$–$C_{10}$-alkyl or $C_1$–$C_8$-alkoxy-$C_1$–$C_6$-alkyl, each of which is optionally substituted by fluorine or chlorine, optionally fluorine-, chlorine-, $C_1$–$C_4$-alkyl- or $C_1$–$C_4$-alkoxy-substituted $C_3$–$C_7$-cycloalky, or represents phenyl, furanyl, pyridyl, imidazolyl, triazolyl, pyrazolyl, pyrimidyl, thiazolyl, thienyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro.

B particularly preferably represents hydrogen or represents $C_1$–$C_{10}$-alkyl or $C_1$–$C_6$-alkoxy-$C_1$–$C_4$-alkyl, each of which is optionally substituted by fluorine or chlorine, or A, B and the linking carbon atom particularly preferably represent saturated or unsaturated $C_5$–$C_8$-cycloalkyl in which optionally one methylene group is replaced by oxygen or sulphur and which is optionally substituted by $C_1$–$C_6$-alkyl, $C_3$–$C_6$-cycloalkyl, $C_1$–$C_3$-halogenoalkyl, $C_1$–$C_6$-alkoxy, $C_1$–$C_6$-alkylthio, fluorine, chlorine or phenyl or A, B and the linking carbon atom particularly preferably represent $C_5$–$C_6$-cycloalkyl or $C_5$–$C_6$-cycloalkenyl in which two substituents together with the linking carbon atoms represent $C_5$–$C_6$-alkanediyl, $C_5$–$C_6$-alkenediyl or $C_6$-alkanedienediyl, each of which is optionally substituted by $C_1$–$C_5$-alkyl, $C_1$–$C_5$-alkoxy, fluorine, chlorine or bromine, and in which optionally one methylene group is replaced by oxygen or sulphur.

G particularly preferably represents hydrogen (a) or one of the groups

(b)

-continued

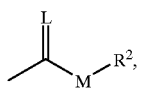  (c)

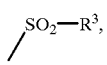  (d)

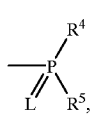  (e)

E or  (f)

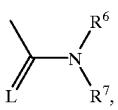  (g)

in which
E represents a metal ion equivalent or an ammonium ion,
L represents oxygen or sulphur and
M represents oxygen or sulphur.

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine or chlorine, or optionally fluorine-, chlorine-, $C_1$–$C_5$-alkyl- or $C_1$–$C_5$-alkoxy-substituted $C_3$–$C_7$-cycloalkyl in which optionally one or two not directly adjacent methylene groups are replaced by oxygen or sulphur, particularly preferably represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, particularly preferably represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, particularly preferably represents pyrazolyl, thiazolyl, pyridyl, pyrimidyl, furanyl or thienyl, each of which is optionally substituted by fluorine, chlorine, bromine or $C_1$–$C_4$-alkyl, particularly preferably represents optionally fluorine-, chlorine-, bromine- or $C_1$–$C_4$-alkyl-substituted phenoxy-$C_1$–$C_5$-alkyl or particularly preferably represents pyridyloxy-$C_1$–$C_5$-alkyl, pyrimidyloxy-$C_1$–$C_5$-alkyl or thiazolyloxy-$C_1$–$C_5$-alkyl, each of which is optionally substituted by -fluorine, chlorine, bromine, amino or $C_1$–$C_4$-alkyl.

$R^2$ particularly preferably represents $C_1$–$C_6$-alkyl, $C_2$–$C_6$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine or chlorine, particularly preferably represents optionally fluorine-, chlorine-, $C_1$–$C_4$-alkyl- or $C_1$–$C_4$-alkoxy-substituted $C_3$–$C_7$-cycloalkyl or particularly preferably represents phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy.

$R^3$ particularly preferably represents optionally fluorine- or chlorine-substituted $C_1$–$C_6$-alkyl or represents phenyl or benzyl, each of which is optionally substituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano or nitro, $R^4$ and $R^5$ independently of one another each particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio or $C_3$–$C_6$-cycloalkylthio, each of which is optionally substituted by fluorine or chlorine, or represent phenyl, phenoxy or phenylthio, each of which is optionally substituted by fluorine, chlorine, bromine, vitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another each particularly preferably represent hydrogen, represent $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_1$–$C_6$-alkyl, each of which is optionally substituted by halogen, represent optionally halogen-, $C_1$–$C_5$-halogenoalkyl-, $C_1$–$C_5$-alkyl- or $C_1$–$C_5$-alkoxy-substituted phenyl, represent optionally halogen-, $C_1$–$C_5$-alkyl-, $C_1$–$C_5$-halogenoalkyl- or $C_1$–$C_5$-alkoxy-substituted benzyl, or together represent a $C_3$-$C_6$-alkylene radical in which optionally one methylene group is replaced by oxygen or sulphur.

X very particularly preferably represents fluorine, chlorine, bromine, methyl, ethyl, propyl, iso-propyl, methoxy, ethoxy, propoxy, iso-propoxy, trifluoromethyl, difluoromethoxy, trifluoromethoxy, nitro or cyano.

Y very particularly preferably represents hydrogen, fluorine, chlorine, bromine, methyl, ethyl, n-propyl, i-propyl, n-butyl, i-butyl, tert-butyl, methoxy, ethoxy, propoxy, iso-propoxy, allyloxy, methallyloxy, trifluoromethyl, difluoromethoxy, trifluoromethoxy, nitro or cyano.

Z very particularly preferably represents fluorine, chlorine, bromine, methyl, ethyl, n-propyl, i-propyl, n-butyl, i-butyl, tert-butyl, methoxy, ethoxy, propoxy, isopropoxy, difluoromethoxy, trifluoromethyl, trifluoromethoxy, nitro or cyano.

n very particularly preferably represents 0, 1, 2 or 3 (in particular represents 0, 1 or 2, specifically represents 0 or 1).

A very particularly preferably represents hydrogen or represents $C_1$–$C_8$-alkyl or $C_1$–$C_6$-alkoxy-$C_1$–$C_4$-alkyl, each of which is optionally substituted by fluorine or chlorine, optionally fluorine-, chlorine-, methyl-, ethyl-, iso-propyl-, tert-butyl-, ethoxy- or methoxy-substituted $C_5$–$C_6$-cycloalkyl, or represents phenyl or benzyl, each of which is optionally substituted by fluorine, chlorine, bromine, methyl, ethyl, iso-propyl, tert-butyl, methoxy, ethoxy, trifluoromethyl, difluoromethoxy, trifluoromethoxy, cyano or nitro.

B very particularly preferably represents hydrogen or represents $C_1$–$C_8$-alkyl or $C_1$–$C_4$-alkoxy-$C_1$–$C_2$-alkyl, each of which is optionally substituted by fluorine, or A, B and the linking carbon atom very particularly preferably represent saturated or unsaturated $C_5$–$C_6$-cycloalkyl in which optionally one methylene group is replaced by oxygen or sulphur and which is optionally substituted by methyl, ethyl, isopropyl, tert-butyl, trifluoromethyl, methoxy, ethoxy, fluorine, chlorine or phenyl or A, B and the linking carbon atom very particularly preferably represent $C_5$–$C_6$-cycloalkyl or $C_5$–$C_6$-cycloalkenyl in which two substituents together with the linking carbon atoms represent $C_5$–$C_6$-alkanediyl, $C_5$–$C_6$-alkenediyl or $C_6$-alkanedienediyl.

G very particularly preferably represents hydrogen (a) or represents one of the groups

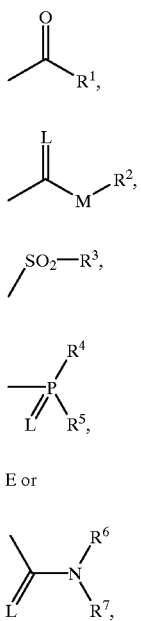

(in particular represents one of the groups (a), (b) or (c)) in which

| E | represents a metal ion equivalent or an ammonium ion, |
| L | represents oxygen or sulphur and |
| M | represents oxygen or sulphur. |

$R^1$ very particularly preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl, each of which is optionally substituted by fluorine or chlorine, or optionally fluorine-, chlorine-, methyl-, ethyl-, propyl-, i-propyl-, butyl-, i-butyl-, tert-butyl-, methoxy-, ethoxy-, propoxy- or iso-propoxy-substituted $C_3$–$C_6$-cycloalkyl in which optionally one or two not directly adjacent methylene groups are replaced by oxygen or sulphur, very particularly preferably represents optionally fluorine-, chlorine-, bromine-, cyano-, nitro-, methyl-, ethyl-, propyl-, i-propyl-, methoxy-, ethoxy-, trifluoromethyl-, trifluoromethoxy-, methylthio-, ethylthio-, methylsulphonyl- or ethylsulphonyl-substituted phenyl, very particularly preferably represents optionally fluorine-, chlorine-, bromine-, methyl-, ethyl-, propyl-, i-propyl-, methoxy-, ethoxy-, trifluoromethyl- or trifluoromethoxy-substituted benzyl, very particularly preferably represents furanyl, thienyl, pyridyl, pyrimidyl, thiazolyl or pyrazolyl, each of which is optionally substituted by fluorine, chlorine, bromine, methyl or ethyl, very particularly preferably represents optionally fluorine-, chlorine-, methyl- or ethyl-substituted phenoxy-$C_1$–$C_4$-alkyl or very particularly preferably represents pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl.

$R^2$ very particularly preferably represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally substituted by fluorine or chlorine, very particularly preferably represents optionally fluorine-, chlorine-, methyl-, ethyl-, propyl-, iso-propyl- or methoxy-substituted $C_3$–$C_6$-cycloalkyl, or very particularly preferably represents phenyl or benzyl, each of which is optionally substituted by fluorine, chlorine, cyano, nitro, methyl, ethyl, propyl, i-propyl, methoxy, ethoxy, trifluoromethyl or trifluoromethoxy.

$R^3$ very particularly preferably represents methyl, ethyl, propyl, isopropyl, each of which is optionally substituted by fluorine or chlorine, or represents phenyl or benzyl, each of which is optionally substituted by fluorine, chlorine, bromine, methyl, ethyl, propyl, iso-propyl, tert-butyl, methoxy, ethoxy, isopropoxy, tert-butoxy, trifluoromethyl, trifluoromethoxy, cyano or nitro, $R^4$ and $R^5$ independently of one another each very particularly preferably represent $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio, each of which is optionally substituted by fluorine or chlorine, or represent phenyl, phenoxy or phenylthio, each of which is optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl.

$R^6$ and $R^7$ independently of one another each very particularly preferably represent hydrogen, represent $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_1$–$C_4$-alkyl, each of which is optionally substituted by fluorine or chlorine, represent optionally fluorine-, chlorine-, bromine-, $C_1$–$C_4$-halogenoalkyl-, $C_1$–$C_4$-alkyl- or $C_1$–$C_4$-alkoxy-substituted phenyl, represent optionally fluorine-, chlorine-, bromine-, $C_1$–$C_4$-alkyl-, $C_1$–$C_4$-halogenoalkyl- or $C_1$–$C_4$-alkoxy-substituted benzyl, or together represent a $C_5$–$C_6$-alkylene radical in which optionally one methylene group is replaced by oxygen or sulphur.

The abovementioned general or preferred radical definitions or illustrations can be combined with each other as desired, i.e. accommodations between the respective ranges and preferred ranges are also possible. They apply both to the end products and, correspondingly, to the precursors and intermediates.

For the purpose of the invention, preference is given to compounds of the formula (I) in which there exists a combination of the meanings mentioned above as being preferred (preferable).

For the purpose of the invention, particular preference is given to compounds of the formula (I) in which there exists a combination of the meanings mentioned above as being particularly preferred.

For the purpose of the invention, very particular preference is given to compounds of the formula (I) in which there exists a combination of the meanings mentioned above as being very particularly preferred.

Saturated or unsaturated hydrocarbon radicals such as alkyl or alkenyl can, as far as possible, in each case be straight-chain or branched, also in combination with heteroatoms, such as, for example, in alkoxy.

Optionally substituted radicals can be mono- or polysubstituted, it being possible in the case of polysubstitution for the substituents to be identical or different.

In addition to the compounds mentioned in the Preparation Examples, the following compounds of the formula (I-1-a) may be specifically mentioned:

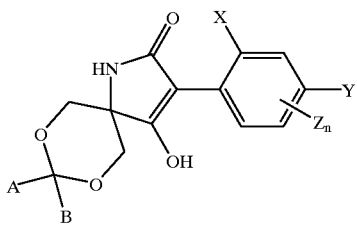

TABLE 1

| X = CH$_3$, Y = H, Z = H. | |
|---|---|
| A | B |
| H | H |
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |
| CF$_3$ | CH$_3$ |
| CF$_3$ | CF$_3$ |
| cyclopropyl | CH$_3$ |
| cyclopentyl | CH$_3$ |
| cyclohexyl | CH$_3$ |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| —(CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi-C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHi-C$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |
| —CH$_2$—CH—(CH$_2$)$_2$—CH—CH$_2$— bridged by —CH$_2$— | |

TABLE 1-continued

| X = CH$_3$, Y = H, Z = H. | |
|---|---|
| A | B |
| —CH$_2$—CH—CH—CH$_2$— bridged by —(CH$_2$)$_4$— | |
| —CH$_2$—CH—CH—(CH$_2$)$_2$— bridged by —(CH$_2$)$_3$— | |
| indane-bridged | |
| tetralin-bridged | |
| C$_6$H$_5$ | H |
| 4-Cl—C$_6$H$_4$ | H |
| C$_6$H$_5$—CH$_2$ | H |
| 4-Cl—C$_6$H$_4$—CH$_2$ | H |

| Table 2: | A and B are each as defined in Table 1<br>X = Cl; Y = H; Z = H |
|---|---|
| Table 3: | A and B are each as defined in Table 1<br>X = CH$_3$; Y = CH$_3$; Z = H |
| Table 4: | A and B are each as defined in Table 1<br>X = CH$_3$; Y = H; Z = 6-CH$_3$ |
| Table 5: | A and B are each as defined in Table 1<br>X = CH$_3$; Y = CH$_3$; Z = 5-CH$_3$ |
| Table 6: | A and B are each as defined in Table 1<br>X = CH$_3$; Y = CH$_3$; Z = 6-CH$_3$ |
| Table 7: | A and B are each as defined in Table 1<br>X = Cl; Y = Cl; Z = H |
| Table 8: | A and B are each as defined in Table 1<br>X = Cl; Y = CH$_3$; Z = H |
| Table 9: | A and B are each as defined in Table 1<br>X = CH$_3$; Y = Cl; Z = H |
| Table 10: | A and B are each as defined in Table 1<br>X = Cl; Y = Cl; Z = 6-CH$_3$ |
| Table 11: | A and B are each as defined in Table 1<br>X = Cl; Y = CH$_3$; Z = Cl |
| Table 12: | A and B are each as defined in Table 1<br>X = CH$_3$; Y = CH$_3$; Z = 6-Cl |
| Table 13: | A and B are each as defined in Table 1<br>X = CH$_3$; Y = Cl; Z = 6-CH$_3$ |
| Table 14: | A and B are each as defined in Table 1<br>X = CH$_3$; Y = CH$_3$; Z = 6-Br |
| Table 15: | A and B are each as defined in Table 1<br>X = CH$_3$; Y = Br; Z = 6-CH$_3$ |
| Table 16: | A and B are each as defined in Table 1<br>X = CH$_3$; Y = Cl; Z = 5-CH$_3$ |
| Table 17: | A and B are each as defined in Table 1<br>X = CH$_3$; Y = Br; Z = 5-CH$_3$ |
| Table 18: | A and B are each as defined in Table 1<br>X = Br; Y = CH$_3$; Z = 5-CH$_3$ |
| Table 19: | A and B are each as defined in Table 1<br>X = Br; Y = Cl, Z = 6-CH$_3$ |
| Table 20: | A and B are each as defined in Table 1<br>X = Br; Y = CH$_3$; Z = 6-Cl |
| Table 21: | A and B are each as defined in Table 1<br>X = Cl, Y = Br; Z = 6-CH$_3$ |

If, according to process (A), methyl N-[(2,4,6-trimethylphenyl]-acetyl-2,2-dimethyl-5-amino-1,3-dioxane-5-carboxylate is used, the course of the process according to the invention can be represented by the following reaction scheme:

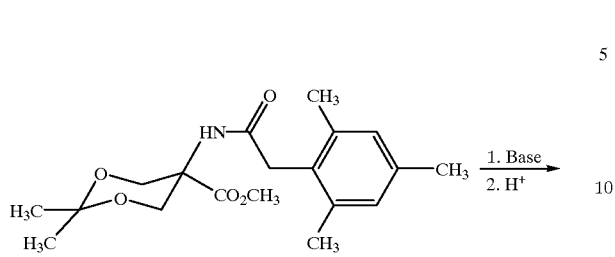

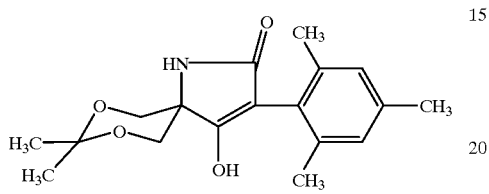

If, according to process (Bα), 3-[(2,4-dichloro)-phenyl]-5,5-(2,4-dioxapentamethylene)-2-pyrrolidine-2,4-dione and pivaloyl chloride are used as starting materials, the course of the process according to the invention can be represented by the following reaction scheme:

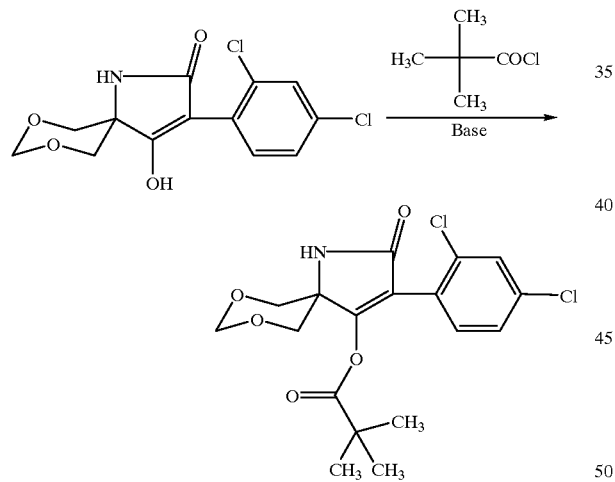

If, according to process (Bβ), cis-3-[(2,4-dimethyl)-phenyl]-5,5-[(3-methyl)-2,4-dioxapentamethylene]-Δ²-pyrrolidine-2,4-dione and acetic anhydride are used as starting material, the course of the process according to the invention can be represented by the following reaction scheme:

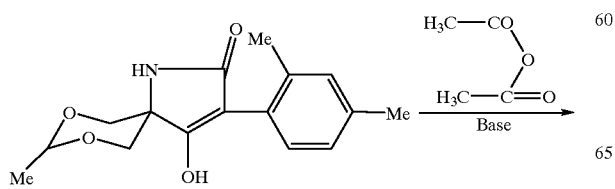

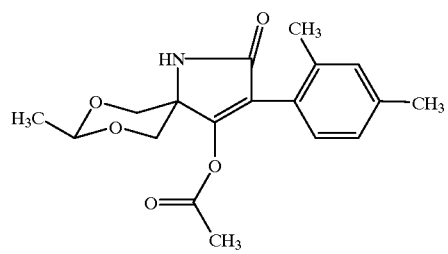

If, according to process (C), 3-[(2,4,5-trimethyl)-phenyl]-5,5-[(3,3-tetramethylene)-2,4-dioxapentamethylene]-Δ²-pyrrolidine-2,4-dione and ethyl chloroformate are used as starting materials, the course of the process according to the invention can be represented by the following reaction scheme:

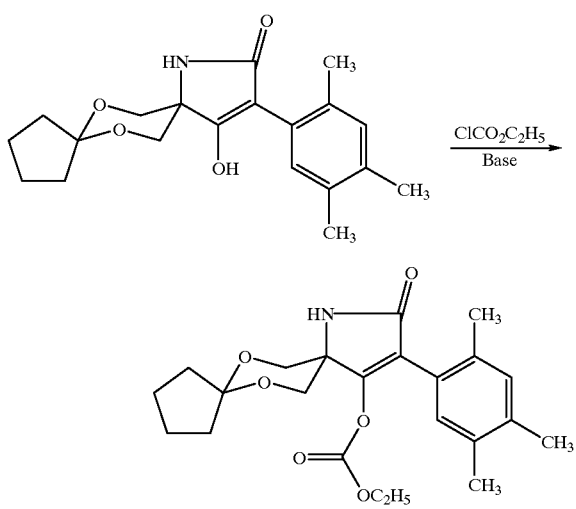

If, according to process (D), trans-3-[(2,6-dimethyl-4-bromo)-phenyl]-5,5-[(3-methyl)-2,4-dioxapentamethylene]-Δ³-pyrrolidine-2,4-dione and methyl chloromonothioformate are used as starting material, the course of the reaction can be represented as follows:

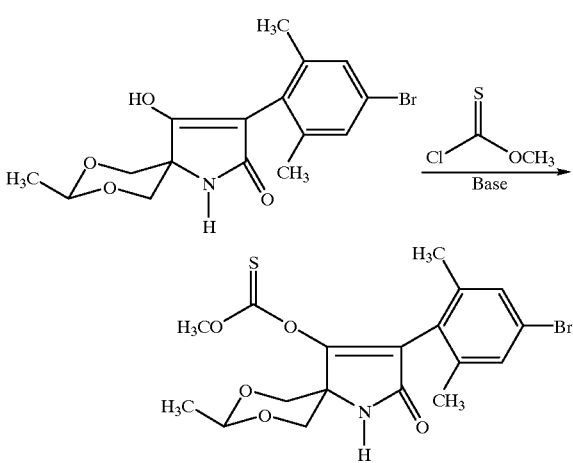

If, according to process (E), 3-[(2-chloro-4-methyl)-phenyl]-5,5-[(3,3-pentamethylene)-2,4-dioxapentamethylene]-Δ³-pyrrolidine-2,4-dione and methane sulphonyl chloride are used as starting materials, the course of the reaction can be represented as follows:

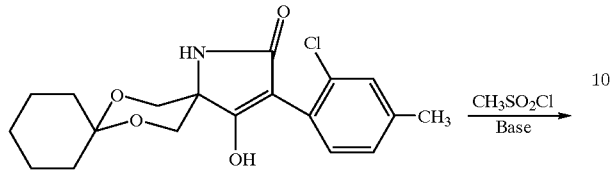

If, according to process (F), 3-[(2,4,6-trimethyl)-phenyl]-5,5-(2,4-dioxapentamethylene)-Δ³-pyrrolidine-2,4-dione and (2,2,2-trifluoromethyl) chloromethanethio-phosphonate are used as starting materials, the course can be represented by the following reaction scheme:

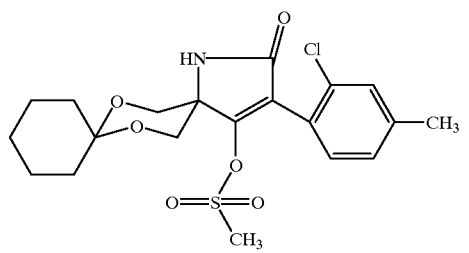

If, according to process (G), 3-[(2,4,6-trimethyl)-phenyl]-5,5-[(3,3-diethylenyloxy)-2,4-dioxapentamethylene]-Δ³-pyrrolidine-2,4-dione and NaOH are used as components, the course of the reaction of the process according to the invention can be represented by the following reaction scheme:

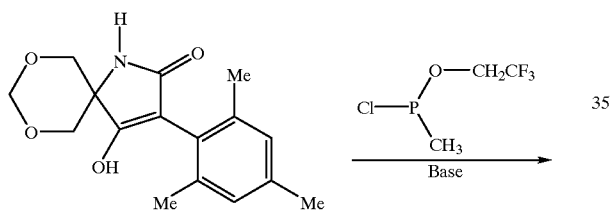

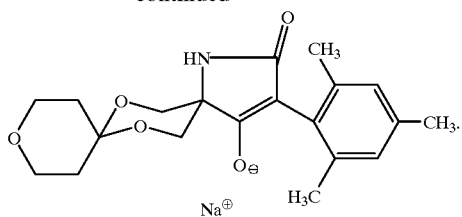

If, according to process (H), 3-[(2-methyl-4-chloro)-phenyl]-5,5-[(3,3-dimethyl)-2,4 dioxapentamethylene]-Δ³-pyrrolidine-2,4-dione and dimethylcarbamoyl chloride are used as starting materials, the course of the reaction can be represented by the following scheme:

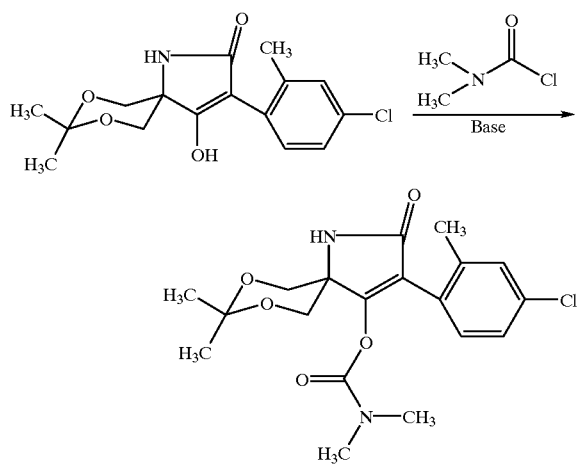

The compounds of the formula (II) required as starting materials in the process (A) according to the invention

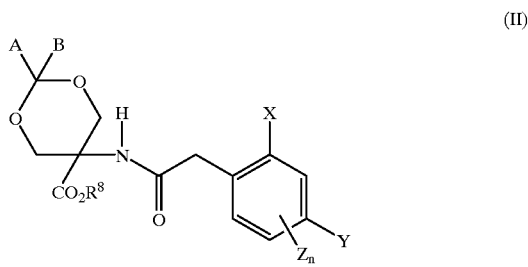

(II)

in which
A, B, D, X, Y, Z, $R^8$ and n are each as defined above, are novel.

The acylamino acid esters of formula (II) are obtained, for example, when amino acid derivatives of the formula (XII)

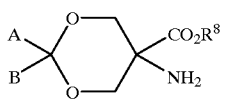

(XII)

in which
A, B and $R^8$ are each as defined above
are acylated with substituted phenylacetyl halides of the formula (XIII)

(XIII)

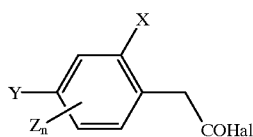

in which

X, Y, Z and n are each as defined above and

Hal represents chlorine or bromine (Chem. Reviews 52, 237–416 (1953); Bhattacharya, Indian J. Chem. 6, 341–5, 1968).

The compounds of the formula (XII) are novel.

The amino acid esters of the formula (XII) are obtained, for example, when nitrocarboxylic esters of the formula (XIV)

(XIV)

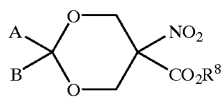

in which

A, B and $R^8$ are each as defined above are reacted with hydrogen in the presence of a hydrogenation catalyst, such as, for example, Raney cobalt or Raney nickel, palladium or platinum (for example on a carbon support), if appropriate in the presence of a diluent, such as, for example, methanol or ethanol, at temperatures between −20° C. and +200° C., preferably between 0° C. and 150° C., and at pressures between 1 bar and 300 bar, preferably between 10 bar and 200 bar (cf. Preparation Examples).

Some of the compounds of the formula (XIV) are known, or they can be prepared by known processes (Piotrowska, Urbanski, Wolochowicz; Bulletin de L'Academie Polonaise des Science XIX, 591–94, 1971).

Furthermore, acylamino esters of the formula (II) are obtained, for example, when amino acid derivatives of the formula (XV)

(XV)

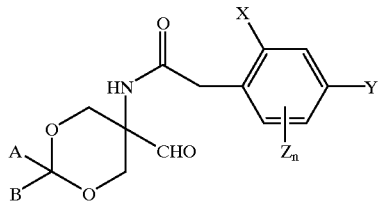

in which

A, B, X, Y, Z and n are each as defined above are oxidized in the presence of a cyanide source, an oxidizing agent and an alcohol, if appropriate in the presence of a solvent.

The compounds of the formula (XV) are novel, but they can be prepared using the method of a known process (Polniaszek, Stevens, J. Org. Chem. 51, 3023–3027, 1986).

The amino acid derivatives of the formula (XV) are obtained, for example, when acyl amino alcohols of the formula (XVI)

(XVI)

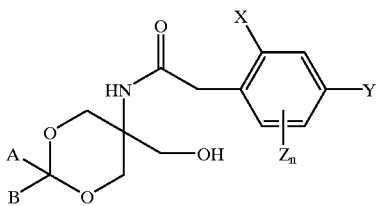

in which

A, B, X, Y, Z and n are each as defined above, are oxidized, for example according to Swern (Polniaszek, Stevens, J. Org. Chem. 51, 3023–3027, 1986; Omura, Swem, Tetrahedron 34, 1951; 1978).

The compounds of the formula (XVI) are novel.

The acylamino alcohols of the formula (XVI) are obtained, for example, when 5-amino-5-hydroxymethyl-1, 3-dioxanes of the formula (XVII)

(XVII)

in which

A and B are each as defined above are acylated with phenyl acetyl halides of the formula (XIII)

(XVII)

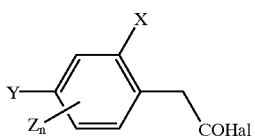

in which

X, Y, Z and n are each as defined above and

Hal represents chlorine or bromine, if appropriate in the presence of a solvent and if appropriate in the presence of a base.

Some of the compounds of the formula (XIII) are novel, but they can be prepared by methods of processes which are known in principle (see Preparation Examples of compounds of the formula XXXIII-b of the German Patent Application DE-19523850).

Some of the compounds of the formula (XVII) are novel.

The amino alcohols of the formula (XVII) are obtained, for example, when nitro alcohols of the formula (XVIII)

(XVIII)

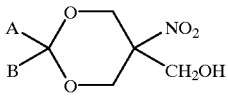

in which

A and B are each as defined above are reacted with hydrogen in the presence of a hydrogenation catalyst, such as, for example, Raney cobalt or Raney nickel, palladium or platinum (for example on a carbon support), if appropriate in the presence of a diluent, such as, for example methanol or ethanol, at temperatures between −20° C. and +200° C., preferably between 0° C. and 150° C., and at pressures between 1 bar and 300 bar, preferably between 10 bar and 200 bar (cf. Preparation Examples).

Some of the nitro alcohols of the formula (XVIII) required as precursors

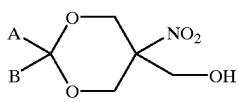

(XVIII)

in which

A and B are as defined above are known, and/or they can be prepared by processes which are known per se (cf. J. Am. Chem. Soc. 63, 2635–2636, (1941); Synthesis 1993, 815–818, WO 95/00020).

Some of the compounds of the formula (XIII) are known, and they can additionally be prepared in accordance with the Patent Applications cited at the outset, or the methods given therein.

The acyl halides of the formula (III), carboxylic anhydrides of the formula. (IV), chloroformic esters or chloroformic thioesters of the formula (V), chloromonothioformic esters or chlorodithioformic esters of the formula (VI), sulphonyl chlorides of the formula (VII), phosphorus compounds of the formula (VIII) and metal hydroxides, metal alkoxides or amines of the formula (IX) and (X) and carbamoyl chlorides of the formula (XI) which are furthermore required as starting materials for carrying out the processes (B), (C), (D), (E), (F), (G) and (H) according to the invention are generally known compounds of organic or inorganic chemistry.

The process (A) is characterized in that compounds of the formula (II) in which A, B, X, Y, Z, n and $R^8$ are each as defined above are subjected to an intramolecular condensation in the presence of a base.

Suitable diluents for the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulphoxide, sulpholane, dimethylformamide and N-methyl-pyrrolidone, and also alcohols such as methanol, ethanol, propanol, iso-propanol, butanol, iso-butanol and tert-butanol.

When carrying out process (A) according to the invention, all customary proton acceptors can be used as base (deprotonating agent). Preference is given to using alkali metal and alkaline earth metal oxides, hydroxides, and carbonates, such as sodium hydroxide, potassium hydroxide, magnesium oxide, calcium oxide, sodium carbonate, potassium carbonate and calcium carbonate, which can also be used in the presence of phase transfer catalysts such as, for example, triethylbenzylammonium chloride, tetrabutylammoniumbromide, Adogen 464 (=methyltrialkyl ($C_8$–$C_{10}$)ammonium chloride) or TDA 1 (=tris-(methoxyethoxyethyl)-amine). Furthermore, alkali metals such as sodium or potassium may be used. Suitable for use are also alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide.

In carrying out the process (A) according to the invention, the reaction temperatures can be varied within a relatively wide range. In general, the reaction is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in approximately equimolar to double-equimolar amounts. However, it is also possible to employ a relatively large excess (up to 3 mol) of one or the other component.

The process (Bα) is characterized in that compounds of the formula (I-a) are reacted with carbonyl halides of the formula (III), if appropriate in the presence of a diluent and if appropriate in the presence of an acid binder.

Suitable diluents for the process (Bα) according to the invention are all solvents which are inert towards the acyl halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, furthermore ketones, such as acetone and methyl isopropyl ketone, nitriles such as acetonitrile, furthermore ethers, such as diethyl ether, tetrahydrofuran and dioxane, additionally carboxylic esters, such as ethyl acetate, and also strongly polar solvents such as dimethyl sulphoxide and sulpholane. The stability of the acyl halide hydrolysis permitting, the reaction can also be carried out in the presence of water.

Suitable acid binders for the reaction according to the process (BαX) according to the invention are all customary acid acceptors. Preference is given to using tertiary amines, such as triethylamine, pyridine, diazabicyclooctane (DABCO), diazabicycloundecene (DBU), diazabicyclononene (DBN), Hunig-Base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate and also alkali metal hydroxides such as sodium hydroxide and potassium hydroxide.

When carrying out the process (Bαx) according to the invention, the reaction temperatures can be varied within a relatively wide range. In general, the reaction is carried out at temperatures between −20° C. and +150° C., preferably between 0° C. and 100° C.

When carrying out the process (Bα) according to the invention, the starting materials of the formula (I-a) and the carbonyl halide of the formula (f) are generally employed in each case in approximately equivalent amounts. However, it is also possible to employ a relatively large excess (up to 5 mol) of the carbonyl halide. Work-up is carried out by customary methods.

The process (Bβ) is characterized in that compounds of the formula (I-a) are reacted with carboxylic anhydrides of the formula (IV), if appropriate in the presence of a diluent and if appropriate in the presence of an acid binder.

Preferred diluents for the process (BB) according to the invention are those diluents which are also preferred when using acyl halides. Otherwise, a carboxylic anhydride which is employed in excess can simultaneously act as a diluent.

Acid binders which may be added in the process (BB) are preferably those acid binders which are also preferred when using acyl halides.

The reaction temperatures in the process (BB) according to the invention can be varied within a relatively wide range.

The reaction is generally carried out between −20° C. and +150° C., preferably between 0° C. and 100° C.

When carrying out the process (Bβ) according to the invention, the starting materials of the formula (I-a) and the carboxylic anhydride of the formula (IV) are generally each employed in approximately equivalent amounts. However, it is also possible to employ a relatively large excess (up to 5 mol) of the carboxylic anhydride. Work-up is carried out by customary methods.

In general, diluent and excess carboxylic anhydride and also the carboxylic acid which is formed are removed by distillation or by washing with an organic solvent or with water.

The process (C) is characterized in that compounds of the formula (I-a) are reacted with chloroformic esters or chloroformic thiol esters of the formula (V), if appropriate in the presence of a diluent and if appropriate in the presence of an acid binder.

Suitable acid binders for the reaction according to the process (C) according to the invention are all customary acid acceptors. Preference is given to using tertiary amines, such as triethylamine, pyridine, DABCO, DBU, DBA, Hünig-Base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate and also alkali metal hydroxides such as sodium hydroxide and potassium hydroxide.

Suitable diluents for the process (C) according to the invention are all solvents which are inert towards the chloroformic esters or chloroformic thiol esters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, nitrites such as acetonitrile, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (C) according to the invention, the reaction temperatures can be varied within a relatively wide range. If the reaction is carried out in the presence of a diluent and an acid binder, the reaction temperatures are generally between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thiol ester of the formula (V) are generally each employed in approximately equivalent amounts. However, it is also possible to employ a relatively large excess (up to 2 mol) of one or the other component. Work-up is carried out by customary methods. In general, precipitated salts are removed and the reaction mixture that remains is concentrated by removing the diluent under reduced pressure.

The process (D) according to the invention is characterized in that compounds of the formula (I-a) are reacted with compounds of the formula (VI) in the presence of a diluent and, if appropriate, in the presence of an acid binder.

In the preparation process (D), approximately 1 mol of chloromonothioformic ester or chlorodithioformic ester of the formula (VI) is reacted per mole of starting material of the formula (I-a) at 0 to 120° C., preferably at 20 to 60° C.

Diluents which may be added, if appropriate, are all inert polar organic solvents, such as ethers, nitrites, ketones, carboxylic esters, amides, sulphones, sulphoxides, but also halogenoalkanes.

Preference is given to using dimethyl sulphoxide, tetrahydrofuran, ethyl acetate, dimethylformamide or methylene chloride.

If, in a preferred embodiment, the enolate salt of the compounds of the formula (I-a) is prepared by addition of strong deprotonating agents such as, for example, sodium hydride or potassium tert-butoxide, the further addition of acid binders can be dispensed with.

If acid binders are used, customary inorganic or organic bases are suitable; sodium hydroxide, sodium carbonate, potassium carbonate, pyridine, triethylamnine may be mentioned by way of example.

The reaction can be carried out at atmospheric pressure or under elevated pressure and is preferably carried out at atmospheric pressure. Work-up is carried out by customary methods.

The process (E) according to the invention is characterized in that compounds of the formula (I-a) are reacted with sulphonyl chlorides of the formula (VII), if appropriate in the presence of a diluent and if appropriate in the presence of an acid binder.

In the preparation process (E), approximately I mol of sulphonyl chloride of the formula (VII) is reacted per mole of starting material of the formula (I-a) at −20 to 150° C., preferably at 20 to 70° C.

Diluents which may be added, if appropriate, are all inert polar organic solvents, such as ethers, amides, ketones, carboxylic esters, nitriles, sulphones, sulphoxides or halogenated hydrocarbons such as methylene chloride.

Preference is given to using dimethylsulphoxide, ethyl acetate, acetonitrile, tetrahydrofuran, dimethylformamide or methylene chloride.

If, in a preferred embodiment, the enolate salt of the compounds (I-a) is prepared by addition of strong deprotonating agents (such as, for example, sodium hydride or potassium tert-butoxide), the further addition of acid binders can be dispensed with.

If acid binders are used, customary inorganic or organic bases are suitable; sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods.

The process (F) according to the invention is characterized in that compounds of the formula (I-a) are in each case reacted with phosphorus compounds of the formula (VIII), if appropriate in the presence of a diluent and if appropriate in the presence of an acid binder.

In the preparation process (F), 1 to 2, preferably 1 to 1.3, mol of the phosphorus compound of formula (VIE) are reacted per mole of the compounds (I-a) at temperatures between 40° C. and 150° C., preferably between −10 and 110° C., to obtain compounds of the formula (I-a).

Diluents which may be added, if appropriate, are all inert polar organic solvents such as ethers, amides, ketones, carboxylic esters, nitriles, alcohols, sulphides, sulphones, sulphoxides, etc.

Preference is given to using acetonitrile, dimethyl sulphoxide, ethyl acetate, tetrahydrofuran, dimethylformamide or methylene chloride.

Acid binders which may be added, if appropriate, are customary inorganic or organic bases such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The resulting end products are preferably purified by crystallization, chromatographic purification or by so-called "incipient distillation", i.e. removal of the volatile components under reduced pressure.

The process (G) is characterized in that compounds of the formula (I-a) are reacted with metal hydroxides or metal alkoxides of the formula (IX) or amines of the formula (X), if appropriate in the presence of a diluent.

Preferred diluents for the process (G) according to the invention are ethers such as tetrahydrofuran, dioxane, diethyl ether or else alcohols such as methanol, ethanol, isopropanol, but also water. The process (G) according to the invention is generally carried out under atmospheric pressure. The reaction temperatures are generally between −20° C. and 100° C., preferably between 0° C. and 50° C.

In preparation process (H), approximately I mol of carbamoyl chloride of the formula (XI) is reacted per mole of starting material of the formula (I-a) at 0 to 150° C., preferably at 20 to 100° C.

Diluents which may be added, if appropriate, are all inert polar organic solvents such as ethers, amides, ketones, carboxylic esters, sulphones, sulphoxides, or halogenated hydrocarbons.

Preference is given to using dimethyl sulphoxide, tetrahydrofuran, ethyl acetate, dimethyl formamide or methylene chloride.

If, in a preferred embodiment, the enolate salt of the compound (I-a) is prepared by addition of strong deprotonating agents (such as, for example, sodium hydride or potassium tert-butylate), the further addition of acid binders can be dispensed with.

If acid binders are used, customary inorganic or organic bases are suitable; sodium hydroxide, sodium carbonate, potassium carbonate, triethylamine and pyridine may be mentioned by way of example.

The reaction can be carried out at atmospheric pressure or under elevated pressure and is preferably carried out at atmospheric pressure. Work-up is carried out by customary methods.

The active compounds are suitable for controlling animal pests, preferably arthropods and nematodes, in particular insects and arachnids, which are encountered in agriculture, in forests, in the protection of stored products and of materials, and in the hygiene sector. They are active against normally sensitive and resistant species and against all or some stages of development. The abovementioned pests include:

From the order of Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., Pediculus humanus corporis, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., *Cono derus* spp., *Melolontha melolontha, Amphimallon solsti tialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyarni, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The active compounds according to the invention have potent insecticidal and acaricidal activity.

They can be used particularly successfully for controlling plant-damaging insects, such as, for example, against the larvae of the mustard beetle (*Phaedon cochleariae*) or against the larvae of the green rice leaf hopper (*Nephotettix cincticeps*) and against the caterpillars of the diamond-back moth (*Plutella maculipennis*).

The active compounds according to the invention can furthermore be used as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthernis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The active compounds according to the invention are highly suitable for the selective control of monocotyledonous weeds in dicotyledonous crops by the pre- and post-emergence methods. They can be employed, for example, very successfully for controlling harmful grasses in cotton or sugar beet.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

If the extender used is water, it is also possible to employ organic solvents, for example, as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; as dispersing agents there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention may be present in its commercial formulations and also in the use forms prepared from these formulations as a mixture with other active compounds, such as insecticides, attractants, sterilants, acaricides, nematicides, fungicides, growth-regulating substances or herbicides. The insecticides include, for example, phosphates, carbamates, carboxylates, chlorinated hydrocarbons, phenyl ureas, substances which are prepared by microorganisms, and the like.

Particularly suitable compounds for mixtures are, for example, those listed below:

Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamates, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforin, triticonazole, validamycin A, vinclozolin, zineb, ziram.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, abamectin, $AC_{303\ 630,}$ acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, beta-cyluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton—S—methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mervinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulphotep, suiprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacrb, varnidothion, XMC, xylylcarb, YI 5301/5302, zetamethrin.

Herbicides:
for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, prirnisulphuron, pyrazosulphuron-ethyl, thifensulphuron-methyl, triasulphuron and tribenuronmethyl; thiolcarbamates such as, for example, butylates, cycloates, di-allates, EPTC, esprocarb, molinates, prosulphocarb, thiobencarb and triallates; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms prepared from these formulations, as a mixture with synergists. Synergists are compounds which increase the action of the active compounds without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp.

They exhibit, for example, excellent activity against Boophilus microplus.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea pigs, rats and mice. By controlling these arthropods, it is intended to reduce mortality and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:
Beetles, such as
*Hylotrupes bajulus, Chlorophorus pilosis, Anobium punctatum, Xestobium rufovillosum, Ptilinus pecticomis,*

*Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*, Xyleborus spec., Tryptodendron spec., *Apate monachus, Bostrychus capucins, Heterobostrychus brunneus*, Sinoxylon spec., *Dinoderus minutus*.

Dermapterans, such as

*Sirex juvencus, Urocerus gigas, Urocerus gigas taicgnus, Urocerus augur.*

Termites, such as

*Kalotermes flavicollis, Cryptotermes brevis, Heterotermes indicola, Reticulitermes flavipes, Reticuliternes santonensis, Reticulitermes lucifugus, Mastotermes darwiniensis, Zootermopsis nevadensis, Coptotermes formosanus.*

Bristletails, such as *Lepisma saccharina*.

Industrial materials are to be understood as meaning, in the present context, non-live materials such as, preferably, synthetic materials, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example: construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably (x-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, known colorants, pigments, water repellents, odour-masking substances and inhibitors or anticorrosives per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the above-mentioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise one or more other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluanide, 3-iodo-2-propinylbutyl carbamate, N-octyl-isothiazolin-3-one and 4,5-dichloro-N-octylisothiazolin-3-one.

The preparation and the use of the active compounds according to the invention is illustrated by the examples below.

PREPARATION EXAMPLES

Example (I-a-1)

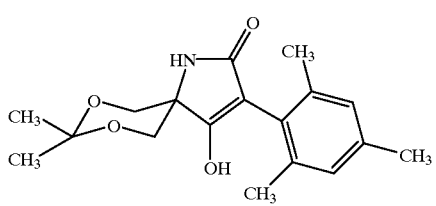

At reflux temperature, 12.5 g (0.0764 mol) of the compound of Example (II-1) in 100 ml of anhydrous toluene are added dropwise to 10 g (0.2 mol) of potassium tert-butoxide in 50 ml of anhydrous tetrahydrofuran (THF), and the mixture is stirred under reflux for 1.5 hours. For work-up, 100 ml of water are added, the aqueous phase is separated off, the toluene phase is extracted with 50 ml of water and the aqueous phases are combined, washed with toluene and acidified at 10 to 20° C. to pH 6 using conc. HCl. The mixture is extracted three times with methylene chloride, the organic phase is dried and concentrated and the residue is chromatographed over silica gel using hexane/acetone 7:3.

Yield: 5.6 g (46% of theory), m.p.: 222–224° C.

Similarly, and according to the general preparation procedures, the following compounds of the formula (I-a) are obtained:

TABLE 22

(I-a)

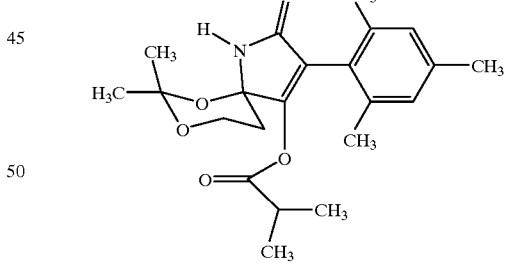

| Ex. No. | X | Y | Z | A | B | m.p. ° C. | isomer |
|---------|---|---|---|---|---|-----------|--------|
| I-a-2 | Cl | Cl | H | $CH_3$ | $CH_3$ | 230 | — |
| I-a-3 | $CH_3$ | $CH_3$ | 6-$CH_3$ | —$(CH_2)_2$—O—$(CH_2)_2$— | | 255 | — |
| I-a-4 | $CH_3$ | $CH_3$ | 6-$CH_3$ | $CH_3$ | H | 182–184 | trans |
| I-a-5 | $CH_3$ | $CH_3$ | 6-$CH_3$ | $CH_3$ | H | 284–285 | cis |
| I-a-6 | $CH_3$ | $CH_3$ | 6-$CH_3$ | —$(CH_2)_4$— | | 245 | — |
| I-a-7 | $CH_3$ | $CH_3$ | 6-$CH_3$ | —$(CH_2)_5$— | | 242 | — |
| I-a-8 | $CH_3$ | $CH_3$ | 6-$CH_3$ | $C_6H_5$ | H | 242 | cis |
| I-a-9 | $CH_3$ | $CH_3$ | 6-$CH_3$ | $H_3CO$—$CH_2$ | H | 256 | n.d. |
| I-a-10 | $CH_3$ | $CH_3$ | 6-$CH_3$ | H | H | >280 | — |

Example (I-b-1)

At 0 to 10° C., 1.2 g (3.75 mmol) of the compound of Example (I-a-1) and 1.1 ml (7.5 mmol) of triethylamine in 50 ml of anhydrous methylene chloride are admixed with 0.8 ml (7.5 mmol) of isobutyryl chloride in 5 ml of anhydrous methylene chloride. The mixture is stirred at room temperature until, according to thin layer chromatography, the reaction has ended. For work-up, the mixture is washed twice with 50 ml of 0.5 N aqueous sodium hydroxide solution, dried over magnesium sulphate and concentrated. The crude product is chromatographed over silica gel using n-hexane/acetone 7:3.

Yield: 0.45 g (31% of theory), m.p.: 153–155° C.

Similarly, and according to the general preparation procedures, the following compounds of the formula (I-b-1) are obtained:

TABLE 23

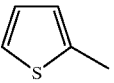

(I-b)

| Ex. No. | X | Y | Z | A | B | R¹ | m.p. ° C. | isomer |
|---|---|---|---|---|---|---|---|---|
| I-b-2 | $CH_3$ | $CH_3$ | 6-$CH_3$ | —$(CH_2)_2$—O—$(CH_2)_2$— | | i-$C_3H_7$— | 210–211 | — |
| I-b-3 | $CH_3$ | $CH_3$ | 6-$CH_3$ | —$(CH_2)_2$—O—$(CH_2)_2$— | | $C_3H_5$— | 228–230 | — |
| I-b-4 | $CH_3$ | $CH_3$ | 6-$CH_3$ | —$(CH_2)_2$—O—$(CH_2)_2$— | | —$C_2H_5$—O—$CH_2$— | 172–174 | — |
| I-b-5 | $CH_3$ | $CH_3$ | 6-$CH_3$ | —$(CH_2)_2$—O—$(CH_2)_2$— | | t-$C_4H_9$—$CH_2$— | 208–210 | — |
| I-b-6 | $CH_3$ | $CH_3$ | 6-$CH_3$ | $CH_3$ | $CH_3$ | 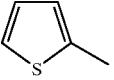 | 195–196 | — |
| I-b-7 | $CH_3$ | $CH_3$ | 6-$CH_3$ | $CH_3$ | $CH_3$ | t-$C_4H_9$—$CH_2$— | 195–196 | — |
| I-b-8 | $CH_3$ | $CH_3$ | 6-$CH_3$ | —$(CH_2)_2$—O—$(CH_2)_2$— | | 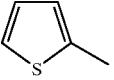 | 230–232 | — |
| I-b-9 | $CH_3$ | $CH_3$ | 6-$CH_3$ | —$(CH_2)_2$—O—$(CH_2)_2$— | | 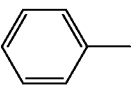 | 240–242 | — |
| I-b-10 | $CH_3$ | $CH_3$ | 6-$CH_3$ | —$(CH_2)_2$—O—$(CH_2)_2$— | | 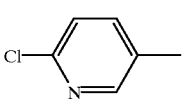 | 210–212 | — |
| I-b-11 | $CH_3$ | $CH_3$ | 6-$CH_3$ | $CH_3$ | H | t-$C_4H_9$—$CH_2$— | 208–210 | trans |
| I-b-12 | $CH_3$ | $CH_3$ | 6-$CH_3$ | $CH_3$ | H | i-$C_3H_7$ | 153–155 | cis |
| I-b-13 | $CH_3$ | $CH_3$ | 6-$CH_3$ | $CH_3$ | H | t-$C_4H_9$—$CH_2$— | 142–144 | cis |
| I-b-14 | $CH_3$ | $CH_3$ | 6-$CH_3$ | —$(CH_2)_4$— | | i-$C_3H_7$ | 197–198 | — |
| I-b-15 | $CH_3$ | $CH_3$ | 6-$CH_3$ | —$(CH_2)_4$— | | t-$C_4H_9$—$CH_2$— | 189–190 | — |
| I-b-16 | $CH_3$ | $CH_3$ | 6-$CH_3$ | $CH_3$ | $CH_3$ | $C_3H_5$- (cyclopropyl) | 204–206 | — |
| I-b-17 | $CH_3$ | $CH_3$ | 6-$CH_3$ | $CH_3$ | H | i-$C_3H_7$— | 188–189 | trans |
| I-b-18 | $CH_3$ | $CH_3$ | 6-$CH_3$ | —$(CH_2)_5$— | | i-$C_3H_7$— | 204–205 | — |
| I-b-19 | $CH_3$ | $CH_3$ | 6-$CH_3$ | —$(CH_2)_5$— | | t-$C_4H_9$—$CH_2$— | 192–194 | — |
| I-b-20 | $CH_3$ | $CH_3$ | 6-$CH_3$ | —$(CH_2)_5$— | | $C_3H_5$— | 196–198 | — |

TABLE 23-continued

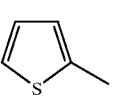

(I-b)

| Ex. No. | X | Y | Z | A | B | R¹ | m.p. ° C. | isomer |
|---|---|---|---|---|---|---|---|---|
| I-b-21 | $CH_3$ | $CH_3$ | 6-$CH_3$ | $C_6H_5$ | H | 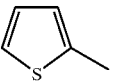 | 248–250 | cis |
| I-b-22 | $CH_3$ | $CH_3$ | 6-$CH_3$ | $C_6H_5$ | H | $i\text{-}C_3H_7$— | 208 | cis |
| I-b-23 | $CH_3$ | $CH_3$ | 6-$CH_3$ | $H_3C$—O—$CH_2$— | H |  | 194–196 | — |
| I-b-24 | $CH_3$ | $CH_3$ | 6-$CH_3$ | $H_3C$—O—$CH_2$— | H | $i\text{-}C_3H_7$— | 146–147 | |
| I-b-25 | $CH_3$ | $CH_3$ | 6-$CH_3$ | $H_3C$—O—$CH_2$— | H | $t\text{-}C_4H$—$CH_2$— | 118–120 | |
| I-b-26 | $CH_3$ | $CH_3$ | 6-$CH_3$ | $H_3C$—O—$CH_2$— | H | 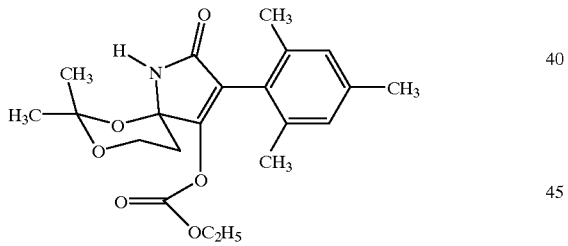 | 180–181 | — |

Example (I-c-1)

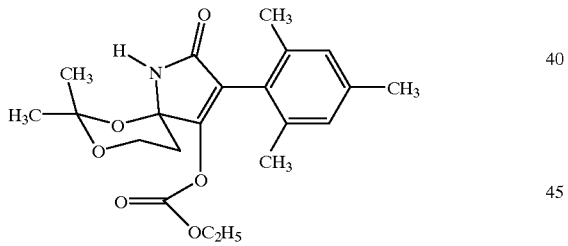

At 0 to 10° C., 0.55 ml (5 mmol) of ethyl chloroformate in 5 ml of anhydrous methylene chloride are added dropwise to 1.2 g (3.75 mmol) of the compound of Example (I-a-1) and 0.8 ml (5.5 mmol) of triethylamine in 50 ml of anhydrous $CH_2Cl_2$, and the reaction mixture is stirred at room temperature until, according to thin layer chromatography, the reaction has ended. For work-up, the mixture is washed twice with 50 ml of 0.5 N aqueous sodium hydroxide solution, dried over magnesium sulphate and concentrated. The residue is chromatographed over silica gel using hexane/acetone 7:3.

Yield: 0.55 g (38% of theory), m.p.: 138–140° C.

Similarly, and according to the general preparation procedures, the following compounds of the formula (I-1-c) are obtained:

TABLE 24

(I-1-c)

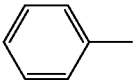

| Ex. No. | X | Y | Z | A | B | L | M | R² | m.p. °C | isomer |
|---|---|---|---|---|---|---|---|---|---|---|
| I-c-2 | CH₃ | CH₃ | 6-CH₃ | —(CH₂)₂—O—(CH₂)₂— | | O | O | C₂H₅ | 228–230 | — |
| I-c-3 | CH₃ | CH₃ | 6-CH₃ | —(CH₂)₂—O—(CH₂)₂— | | O | O | 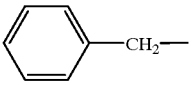 | 226–228 | — |
| I-c-4 | CH₃ | CH₃ | 6-CH₃ | —(CH₂)₂—O—(CH₂)₂— | | O | O | C₆H₅—CH₂— | 170–172 | — |
| I-c-5 | CH₃ | CH₃ | 6-CH₃ | CH₃ | H | O | O | C₂H₅ | 182–184 | trans |
| I-c-6 | CH₃ | CH₃ | 6-CH₃ | CH₃ | H | O | O | C₂H₅ | glass-like oil | cis |
| I-c-7 | CH₃ | CH₃ | 6-CH₃ | —(CH₂)₄— | | O | O | C₂H₅ | 141–143 | — |
| I-c-8 | CH₃ | CH₃ | 6-CH₃ | —(CH₂)₅— | | O | O | C₂H₅ | 195 | — |
| I-c-9 | CH₃ | CH₃ | 6-CH₃ | H₃CO—CH₂— | H | O | O | C₂H₅ | 166–168 | — |
| I-c-10 | CH₃ | CH₃ | 6-CH₃ | C₆H₅— | H | O | O | C₂H₅ | 207 | |

Example (I-d-1)

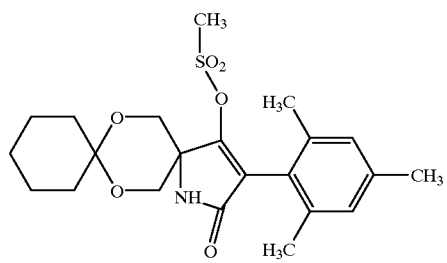

At 0° C., 3.6 g of the compound of Example (I-a-7) in 50 ml of methylene chloride and 1.5 ml of triethylamine are admixed with 0.8 ml of mesyl chloride in 5 ml of methylene chloride, and the mixture is stirred without cooling for 1 day. Silica gel chromatography gives 2.50 g (58% of theory), m.p.: 212–214° C.

Example (I-f-1)

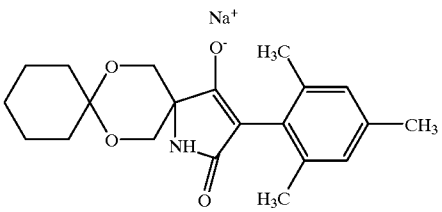

At 20° C., 3.6 g of the compound of Example (I-a-7) in 50 ml of methanol are admixed with 2 g of sodium methoxide solution and stirred at this temperature for one day. The mixture is then admixed with toluene and evaporated under reduced pressure. Yield: 4.50 g (99% of theory), m.p.: >250° C.

Example (I-2-1)

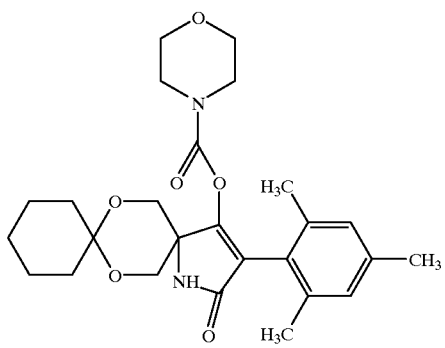

At reflux temperature, 3.6 g of the compound of Example (I-a-7) in 50 ml of ethyl acetate and 1.5 ml of triethylamine are admixed with 1.4 g of morpholinecarbamoyl chloride in 5 ml of ethyl acetate, and the mixture is heated under reflux for one day. Silica gel chromatography gives 0.85 g (18% of theory), m.p.: 190–192° C.

Example (II-1)

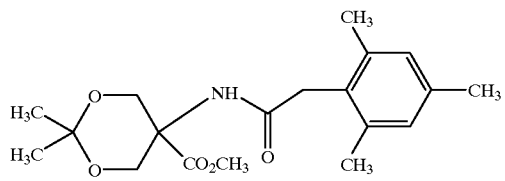

Under argon, 102 g (0.63 mol) of the compound of Example (XV-1) in 1200 ml of methylene chloride were admixed under argon with 54 g of acetone cyanohydrin and 10.5 ml of triethylamine, and the mixture was stirred at 20° C. for one day and concentrated (reagent A). 46.5 g of oxalyl chloride were initially charged in 600 ml of methylene chloride. 81 g of dimethyl sulphoxide in 210 ml of methylene chloride were added dropwise to this mixture at −78° C. After 15 minutes, reagent A (aldehyde cyanohydrin) dissolved in 450 ml of methylene chloride is added dropwise at −78° C., and the mixture is stirred at −78° C. for 30 minutes and then at −25° C. for 30 minutes. The mixture is once more cooled to −78° C., and 230 ml of triethylamine are added dropwise. The mixture is subsequently stirred at −78° C. for 10 minutes. After warming to −25° C., the mixture is admixed with 1050 ml of methanol and stirred at room temperature for one day. The reaction mixture is poured into water, extracted with methylene chloride and the organic phase is dried and concentrated. Silica gel chromatography using n-hexane/acetone 7:3 and crystallization using methylene chloride/n-hexane gives 43 g of the above-mentioned ester (19% of theory) of melting point 106° C.

Similarly to Example (II-1), and in accordance with the general preparation procedures, the following compounds of the formula (II) are prepared.

TABLE 25

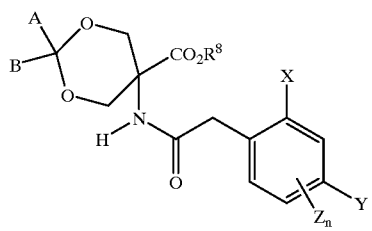

(II)

| Ex. No. | X | Y | Z | A | B | $R^8$ | m.p. ° C. | isomer |
|---|---|---|---|---|---|---|---|---|
| II-2 | Cl | Cl | H | $CH_3$ | $CH_3$ | $CH_3$ | 183 | |
| II-3 | $CH_3$ | $CH_3$ | 6-$CH_3$ | —$(CH_2)_2$—O—$(CH_2)_2$— | | $CH_3$ | 135 | |
| II-4 | $CH_3$ | $CH_3$ | 6-$CH_3$ | $CH_3$ | H | $CH_3$ | 152 | trans |
| II-5 | $CH_3$ | $CH_3$ | 6-$CH_3$ | $CH_3$ | H | $CH_3$ | *1) | cis |
| II-6 | $CH_3$ | $CH_3$ | 6-$CH_3$ | —$(CH_2)_4$— | | $CH_3$ | 98 | |
| II-7 | $CH_3$ | $CH_3$ | 6-$CH_3$ | —$(CH_2)_5$— | | $CH_3$ | 108 | |
| II-8 | $CH_3$ | $CH_3$ | 6-$CH_3$ | $C_6H_5$ | H | $CH_3$ | *2) | cis |
| II-9 | $CH_3$ | $CH_3$ | 6-$CH_3$ | H | H | $CH_3$ | 130–132 | — |
| II-10 | $CH_3$ | $CH_3$ | 6-$CH_3$ | $H_3C$—O—$CH_2$— | H | $CH_3$ | 60–62 | |

*1) 400 MHz in $d_6$-DMSO: δ = 3.93(d, 2H, O—$CH_2$), 4.08(d, 2H, O$CH_2$), 4.86(q, 1H, CHMe)
*2) was cyclized to (I-a-8) without any further purification Example (XV-1)

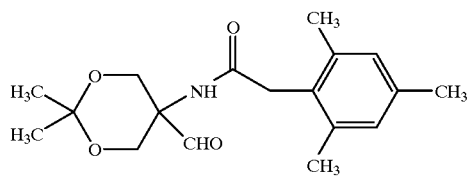

At −70° C., 19 mil of DMSO are added dropwise to 20 ml of oxalyl chloride in 1000 ml of anhydrous tetrahydrofuran, the mixture is stirred at −35° C. for 3 minutes and cooled again to −70° C., and 65 g (0.25 mol) of the compound of Example XVI-1 in 300 ml of anhydrous tetrahydrofuran are added dropwise over a period of 1 hour. The mixture is stirred at −35° C. for 15 minutes, 250 ml of triethylamine are added dropwise and the mixture is stirred at room temperature for one day. The mixture is admixed with n-hexane, the precipitate is filtered off, the filtrate is concentrated using a rotary evaporator and the residue is chromatographed over silica gel using methylene chloride/acetone 2:1.

Yield: 44.5 g (Δ67% of theory) of m.p.: 110° C.

Similarly to Example (XV-1), and according to the general procedures, the following compounds of the formula (XV) were prepared.

TABLE 26

(XV)

| Ex. No. | X | Y | Z | A | B | m.p. ° C. | isomer |
|---|---|---|---|---|---|---|---|
| XV-2 | Cl | Cl | H | CH₃ | CH₃ | 130 | — |
| XV-3 | CH₃ | CH₃ | 6-CH₃ | —(CH₂)₂—O—(CH₂)₂— | | 130 | — |
| XV-4 | CH₃ | CH₃ | 6-CH₃ | CH₃ | H | >240 | trans |
| XV-5 | CH₃ | CH₃ | 6-CH₃ | CH₃ | H | 151 | cis |
| XV-6 | CH₃ | CH₃ | 6-CH₃ | —(CH₂)₄— | | 120 | — |
| XV-7 | CH₃ | CH₃ | 6-CH₃ | —(CH₂)₅— | | 155 | — |
| XV-8 | CH₃ | CH₃ | 6-CH₃ | C₆H₅— | H | >260 | cis |
| XV-9 | CH₃ | CH₃ | 6-CH₃ | H₃C—O—CH₂— | H | 112–114 | |
| XV-10 | CH₃ | CH₃ | 6-CH₃ | H | H | *1) | |

*1)was reacted as crude product to give (II-9)

Example (XVI-1)

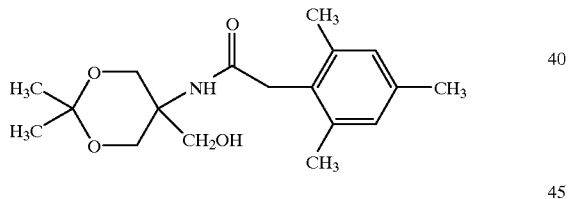

45 g (0.25 mol) of the compound of Example XVII-1 are dissolved in 500 ml of anhydrous tetrahydrofuran and admixed with 40 ml of triethylamine, 50 g of misitylene acetyl chloride are added dropwise at 0° C. and the mixture is stirred at room temperature for 1 h. The precipitate is filtered off, the filtrate is concentrated and the residue is chromatographed over silica gel using hexane/ethyl acetate 2:1.

Yield: 66 g (Δ82% of theory) of melting point 94° C.

Similarly to Example XVI-1, and according to the general procedures, the following compounds of the formula XVI were prepared.

TABLE 27

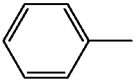

(XV)

| Ex. No. | X | Y | Z | A | B | m.p. °C. | isomer |
|---|---|---|---|---|---|---|---|
| XVI-2 | Cl | Cl | H | CH$_3$ | CH$_3$ | 100 | — |
| XVI-3 | CH$_3$ | CH$_3$ | 6-CH$_3$ | —(CH$_2$)$_2$—O—(CH$_2$)$_2$— | | 168 | — |
| XVI-4 | CH$_3$ | CH$_3$ | 6-CH$_3$ | CH$_3$ | H | 97 | trans |
| XVI-5 | CH$_3$ | CH$_3$ | 6-CH$_3$ | CH$_3$ | H | viscous oil | cis |
| XVI-6 | CH$_3$ | CH$_3$ | 6-CH$_3$ | —(CH$_2$)$_4$— | | 104 | — |
| XVI-7 | CH$_3$ | CH$_3$ | 6-CH$_3$ | —(CH$_2$)$_4$— | | 132 | — |
| XVI-8 | CH$_3$ | CH$_3$ | 6-CH$_3$ | phenyl | H | 813 | cis |
| XVI-9 | CH$_3$ | CH$_3$ | 6-CH$_3$ | CH$_3$—O—CH$_2$— | H | 58–60 | |
| XVI-10 | CH$_3$ | CH$_3$ | 6-CH$_3$ | H | H | *1) | |

*1)was reacted as crude product to give (XV-10).

Example (XVII-1)

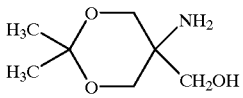

13.5 g (0,07 mol) of 5-amino-2,2-dimethyl-5-hydroxymethyl-1,3-dioxane in 100 ml of ethanol are hydrogenated at 40° C. in an autoclave in the presence of 2 g of Raney nickel using hydrogen at 20 bar. The catalyst is filtered off, the filtrate is concentrated, the residue is taken up in methylene chloride and the product is precipitated with n-hexane.

Yield: 10.3 g (=91% of theory)

$^1$H-NMR (200 MHz in d$_6$-DMSO):δ=1.28 (s, 3H, CH$_3$), 1.32 (s, 3H, CH$_3$), 3.35 (s, 2H, CH$_2$OH), 3.4 (d, 2H, OCH$_2$), 3.57 (d, 2H, OCH$_2$)

Example (XVIII-1)

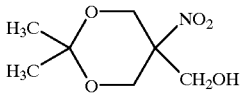

100 g of 2,2-dimethoxypropane are dissolved in 1000 ml of acetone, 5 g of p-toluene sulphonic acid are added, 150 g of trishydroxymethylnitromethane are introduced and the mixture is stirred at room temperature for 1 h. After the addition of a further 100 g of 2,2-dimethoxypropane, the mixture is heated at 40° C. for 4 h and then concentrated, and the residue is chromatographed over silica gel using hexane/acetone 7:3.

Yield: 75 g (=39% of theory)

$^1$H-NMR (200 MHz in d$_6$-DMSO):δ=1.23 (s, 3H, CH$_3$), 1.28 (s, 3H, CH$_3$), 3.7 (d, 2H, CH$_2$OH), 4.02 (d, 2H, OCH$_2$), 4.32 (d, 2H, OCH$_2$)

The cis/trans isomer mixtures of compounds of the formula XVIII which are obtained when aldehydes are used are separated into the isomers by crystallization, chromatographic methods or distillation.

USE EXAMPLES

Example A

Tetranychus Test (OP-resistant/dip treatment)

| | |
|---|---|
| Solvent: | 7.5 parts by weight of dimethylformamide |
| | 100 parts by weight of methanol |
| Emulsifier: | 2.5 parts by weight of alkylaryl polyglycol ether |

To produce a suitable preparation of active compound, I part by weight of active compound is mixed with the stated amount of emulsifier, and the concentrate is diluted with water with emulsifier-containing water to the desired concentrations.

Bean plants (*Phaseolus vulgaris*), which are heavily infested by all stages of the greenhouse red spider mite *Tetranychus urticae*, are dipped into a preparation of active compound of the desired concentration.

After the desired period of time, the effect in % is determined. 100% means that all spider mites have been killed; 0% means that none of the spider mites have been killed.

In this test, at an exemplary active compound concentration of 0.1%, for example, the compounds of preparation examples I-a-1, I-b-1 and I-c-1 show a kill of ≧98% after 13 d.

Example B

| Phaedon-Larvae Test | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with mustard beetle larvae (*Phaedon cochleariae*) while the leaves are still moist.

After the desired period of time, the kill n % is determined. 100% means that all beetle larvae have been killed; 0% means that none of the beetle larvae have been killed.

In this test, at an exemplary active compound concentration of 0.1%, for example, the compounds of preparation examples activity I-a-1, I-b-1, I-b-2-, I-b-3, I-a-4 and I-b-10 show a kill of 100% after 7 days.

Example C

| Plutella Test | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the diamond-back moth (*Plutella maculipennis*) while the leaves are still moist.

After the desired period of time, the kill n % is determined. 100% means that all caterpillars have been killed; 0% means that none of the caterpillars have been killed.

In this test, at an exemplary active compound concentration of 0.1%, for example, the compounds of preparation examples activity I-a-1, I-b-1 and I-c-1 show a kill of 100% after 7 days.

Example D

| Nephotettix Test | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are populated with larvae of the green rice leaf hopper (*Nephotettix cincticeps*) while the seedlings are still moist.

After the desired period of time, the kill n % is determined. 100% means that all leaf hoppers have been killed; 0% means that none of the leaf hoppers have been killed.

In this test, at an exemplary active compound concentration of 0.1%, for example, the compounds of preparation examples I-a-1, I-b-1, I-c-1, I-b-2, I-c-2, I-a-4, I-b-8 and I-c-4 show a kill of 100% after 6 days.

Example E

| Spodoptera Test | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the owlet moss (*Spodoptera frugiperda*) while the leaves are still moist.

After the desired period of time, the kill n % is determined. 100% means that all caterpillars have been killed; 0% means that none of the caterpillars have been killed.

In this test, at an exemplary active compound concentration of 0.1%, for example, the compounds of preparation examples I-b-2, I-a-4, I-b-8 and I-b-10 show a kill of $\geq 90\%$ after 7 days.

Example F

| Myzus Test | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage plants (*Brassica oleracea*) which are heavily infested by peach aphids (*Myzus persicae*) are treated by being dipped into the preparation of active compound of the desired concentration.

After the desired period of time, the kill n % is determined. 100% means that all aphids have been killed; 0% means that none of the aphids have been killed.

In this test, at an exemplary active compound concentration of 0.1%, for example, the compounds of preparation examples I-a-1, I-a-3, I-b-2, I-c-2, I-a-4 and I-c-4 show a kill of $\geq 90\%$ after 6 days.

What is claimed is:

1. A compound of the formula (I)

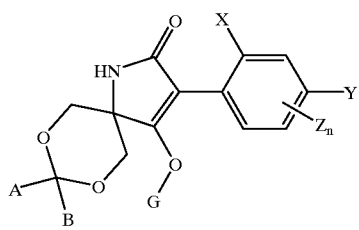

wherein

X represents halogen, alkyl, alkenyl, alkynyl, alkoxy, alkenyloxy, alkylthio, alkylsulphinyl, alkylsulphonyl, halogenoalkyl. halogenoalkenyl, halogenoalkoxy, halogenoalkenyloxy, nitro, cyano or represents phenyl, phenoxy, phenylthio, benzyloxy or benzylthio, each of which is unsubstituted or substituted, Y represents hydrogen, halogens alkyl, alkenyl, alkynyl, alkoxy, alkenyloxy, alkylthio, alkylsulphinyl, alkylsulphonyl, halogenoalkyl, halogenoalkenyl, halogenoalkoxy, halogenoalkenyloxy, nitro or cyano, Z represents halogen, alkyl, alkenyl, alkynyl, halogenoalkyl, halogenoalkenyl, alkoxy, alkenyloxy, halogenoalkoxy, halogenoalkenyloxy, nitro or cyano, n represents 0, 1, 2 or 3, A represents hydrogen, represents alkyl, alkenyl, alkynyl, alkoxyalkyl, polyalkoxyalkyl or alkylthioalkyl, each of which is unsubstituted or substituted by halogen, represents saturated or unsaturated cycloalkyl which is unsubstituted or substituted and wherein zero or at least one ring atom is replaced by a heteroatom, or represents aryl, arylalkyl or hetaryl, each of which is unsubstituted or substituted by halogen, alkyl, halogenoalkyl, alkoxy, halogenoalkoxy, cyano or nitro and which is unsubstituted or substituted by substituted phenoxy, benzyloxy or hetaryloxy, B represents hydrogen or represents alkyl or alkoxyalkyl, each of which is unsubstituted or substituted by halogen, or A and B together with the linking carbon atom represent a saturated or unsaturated, unsubstituted or substituted ring which contains zero or one heteroatom.

G represents hydrogen (a) or represents one of the groups

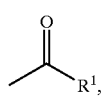

(b)

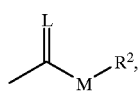

(c)

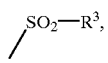

(d)

(e)

E or (f)

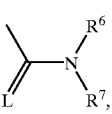

(g)

wherein

E represents a metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyalkyl, each of which is unsubstituted or substituted by halogen, or represents unsubstituted or halogen-, alkyl- or alkoxy-substituted cycloalkyl which is interrupted by zero or at least one heteroatom or represents phenyl, phenylalkyl, hetaryl, phenoxyalkyl or hetaryloxyalkyl, each of which is unsubstituted or substituted, $R^2$ represents alkyl, alkenyl, alkoxyalkyl or polyalkoxyalkyl, each of which is unsubstituted or substituted by halogen, or represents cycloalkyl, phenyl or benzyl, each of which is unsubstituted or substituted, $R^3$, $R^4$ and $R^5$ independently of one another each represent alkyl, alkoxy, alkylamino, dialkylamino, alkylthio, alkenylthio or cycloalkylthio, each of which is unsubstituted or substituted by halogen, or represents phenyl, benzyl, phenoxy or phenylthio, each of which is unsubstituted or substituted, and $R^6$ and $R^7$ independently of one another each represents hydrogen, represents alkyl, cycloalkyl, alkenyl, alkoxy or alkoxyalkyl, each of which is unsubstituted or substituted by halogen, represents unsubstituted or substituted phenyl, represents unsubstituted or substituted benzyl, or together with the linking N atom represents an optionally by oxygen or sulphur containing ring.

2. A compound of the formula (I) according to claim 1 wherein x represents halogen, $C_1$–$C_6$-alkyl, $C_2$–$C_6$-alkenyl, $C_2$–$C_6$-alkynyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro, cyano or represents phenyl, phenoxy, phenylthio, benzyloxy or benzylthio, each of which is unsubstituted or substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, Y represents hydrogen, halogen, $C_1$–$C_6$-alkyl, $C_2$–$C_6$-alkenyl, $C_2$–$C_6$-alkynyl, $C_1$–$C_6$-alkoxy, $C_3$–$C_6$-alkenyloxy, $C_1$–$C_6$-alkylthio, $C_1$–$C_6$-alkylsulphinyl, $C_1$–$C_6$-alkylsulphonyl, $C_1$–$C_6$-halogenoalkyl, $C_2$–$C_6$-halogenoalkenyl, $C_1$–$C_6$-halogenoalkoxy, $C_3$–$C_6$-halogenoalkenyloxy, nitro or cyano, Z represents halogen, $C_1$–$C_6$-alkyl, $C_2$–$C_6$-alkenyl, $C_2$–$C_6$-alkynyl, $C_1$–$C_6$-halogenoalkyl, $C_2$–$C_6$-halogenoalkenyl, $C_1$–$C_6$-alkoxy, $C_3$–$C_6$-alkenyloxy, $C_1$–$C_6$-halogenoalkoxy, $C_3$–$C_6$-halogenoalkenyloxy, nitro or cyano, n represents 0, 1, 2 or 3, A represents hydrogen or represents $C_1$–$C_{12}$-alkyl, $C_2$–$C_8$-alkenyl, $C_2$–$C_8$-alkynyl, $C_1$–$C_{10}$-alkoxy-$C_1$–$C_8$-alkyl, poly-$C_1$–$C_6$-alkoxy-$C_1$–$C_8$-alkyl or $C_1$–$C_{10}$-alkylthio-$C_1$–$C_6$-alkyl, each of which is unsubstituted or substituted by halogen, represents unsubstituted or halogen-, $C_1$–$C_6$-alkyl- or $C_1$–$C_6$-alkoxy-substituted $C_3$–$C_8$-cycloalkyl in which zero or one methylene group is replaced by oxygen or sulphur or represents phenyl or naphthyl, hetaryl having 5 to 6 ring atoms, furanyl, pyridyl, imidazolyl, triazolyl, pyrazolyl, pyrimidyl, thiazolyl or thienyl or phenyl- or naphthyl-$C_1$–$C_6$-alkyl, each of which is unsubstituted or substituted by one or more substituents selected from the group consisting of halogen, $C_1$–$C_6$-alkyl, $C_1$–$C_6$-halogenoalkyl, $C_1$–$C_6$-alkoxy, $C_1$–$C_6$-halogenoalkoxy, cyano, nitro, and unsubstituted or halogen-, $C_1$–$C_4$-alkyl-, $C_1$–$C_4$-alkoxy-, $C_1$–$C_2$-halogenoalkyl-, $C_1$–$C_2$-halogenoalkoxy-, cyano- or nitro-substituted phenoxy, B represents hydrogen or represents $C_1$–$C_{12}$-alkyl or $C_1$–$C_8$-alkoxy-$C_1$–$C_6$-alkyl, each of which is unsubstituted or substituted by halogen, or A, B and the linking carbon atom represent saturated or unsaturated $C_3$–$C_{10}$ cycloalkyl, wherein zero or one methylene group is replaced by oxygen or sulphur and which is unsubstituted or mono- or polysubstituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the linking carbon atom represent $C_5$–$C_8$-cycloalkyl or $C_5$–$C_8$ cycloalkenyl, in which two substituents together with the linking carbon atoms represent $C_5$–$C_6$-alkanediyl, $C_5$–$C_6$-alkenediyl or $C_6$-alkanedienediyl, each of which is unsubstituted or substituted by $C_1$–$C_6$-alkyl, $C_1$–$C_6$-alkoxy or halogen and wherein zero or one methylene group is replaced by oxygen or sulphur, G represents hydrogen (a) or represents one of the groups

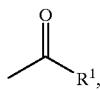
(b)

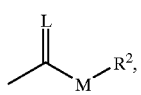
(c)

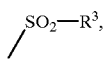
(d)

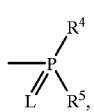
(e)

(f)

E or

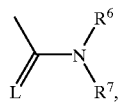
(g)

wherein
E represents a metal ion equivalent or an ammonium ion,
L represents oxygen or sulphur and
M represents oxygen or sulphur, $R^1$ represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is unsubstituted or substituted by halogen, or represents unsubstituted or halogen-, $C_1$–$C_6$-alkyl- or $C_1$–$C_6$-alkoxy-substituted $C_3$–$C_8$-cycloalkyl, in which zero or at least one methylene group is replaced by oxygen or sulphur, represents unsubstituted or halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents unsubstituted or halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, represents unsubstituted or halogen- or $C_1$–$C_6$-alkyl-substituted 5- or 6-membered hetaryl, represents unsubstituted or halogen- or $C_1$–$C_6$-alkyl-substituted phenoxy-$C_1$–$C_6$-alkyl or represents unsubstituted or halogen-, amino- or $C_1$–$C_6$-alkyl-substituted 5- or 6-membered hetaryloxy-$C_1$–$C_6$-alkyl, $R^2$ represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is unsubstituted or substituted by halogen, represents unsubstituted or halogen-, $C_1$–$C_6$-alkyl- or $C_1$–$C_6$-alkoxy-substituted $C_3$–$C_8$-cycloalkyl or represents phenyl or benzyl, each of which is unsubstituted or substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy, $R^3$ represents unsubstituted or halogen-substituted $C_1$–$C_8$-alkyl or represents phenyl or benzyl, each of which is unsubstituted or substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ and $R^5$ independently of one another each represents $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio or $C_3$–$C_7$-cycloalkylthio, each of which is unsubstituted or substituted by halogen, or represent phenyl, phenoxy or phenylthio, each of which is unsubstituted or substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl and $R^6$ and $R^7$ independently of one another each represents hydrogen, represents $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_1$–$C_8$-alkyl, each of which is unsubstituted or substituted by halogen, represents unsubstituted or halogen-, $C_1-C_8$-halogenoalkyl-, $C_1-C_8$-alkyl- or $C_1-C_8$-alkoxy-substituted phenyl, unsubstituted or halogen-, $C_1-C_8$-alkyl-, $C_1-C_8$-halogenoalkyl- or $C_1-C_8$-alkoxy-substituted benzyl or together represent a $C_3-C_6$-alkylene radical in which zero or one methylene group is replaced by oxygen or sulphur.

3. A compound of the formula (1) according to claim 1 wherein

X represents fluorine, chlorine, bromine, $C_1-C_4$-alkyl, $C_1-C_4$-alkoxy, $C_1-C_4$-halogenoalkyl, $C_1-C_4$-halogenoalkoxy, nitro, cyano or represents phenyl or benzyloxy, each of which is unsubstituted or substituted by fluorine, chlorine, bromine, $C_1-C_4$-alkyl, $C_1-C_4$-alkoxy, $C_1-C_2$-halogenoalkyl, $C_1-C_2$-halogenoalkoxy, nitro or cyano, Y represents hydrogen, fluorine, chlorine, bromine, $C_1-C_4$-alkyl, $C_1-C_4$-alkoxy, $C_3-C_4$-alkenyloxy, $C_1-C_4$-halogenoalkyl, $C_1-C_4$-halogenoalkoxy, nitro or cyano, Z represents fluorine, chlorine, bromine, $C_1-C_4$-alkyl, $C_1-C_4$-halogenoalkyl, $C_1-C_4$-alkoxy, $C_1-C_4$-halogenoalkoxy, nitro or cyano, n represents 0, 1, 2 or 3, A represents hydrogen or represents $C_1-C_{10}$-alkyl or $C_1-C_8$-alkoxy-$C_1-C_1$-alkyl, each of which is unsubstituted or substituted by fluorine or chlorine, unsubstituted or fluorine-, chlorine-, $C_1-C_4$-alkyl- or $C_1-C_4$-alkoxy-substituted $C_3-C_7$-cycloalkyl, or represents phenyl, furanyl, pyridyl, imidazolyl, triazolyl, pyrazolyl, pyrimidyl, thiazolyl, thienyl or phenyl-$C_1-C_4$-alkyl, each of which is unsubstituted or substituted by fluorine, chlorine, bromine, $C_1-C_4$-alkyl, $C_1-C_4$-halogenoalkyl, $C_1-C_4$-alkoxy, $C_1-C_4$-halogenoalkoxy, cyano or nitro, B represents hydrogen or represents $C_1-C_{10}$-alkyl or $C_1-C_6$-alkoxy-$C_1-C_4$-alkyl, each of which is unsubstituted or substituted by fluorine or chlorine, or A, B and the linking carbon atom represent saturated or unsaturated $C_5-C_8$-cycloalkyl in which zero or one methylene group is replaced by oxygen or sulphur and which is unsubstituted or substituted by $C_1-C_6$-alkyl, $C_3-C_8$-cycloalkyl, $C_1-C_3$-halogenoalkyl, $C_1-C_6$-alkoxy, $C_1-C_6$-alkylthio, fluorine, chlorine or phenyl or A, B and the linking carbon atom represent $C_5-C_6$-cycloalkyl or $C_5-C_6$-cycloalkenyl in which two substituents together with the linking carbon atoms represent $C_5-C_6$-alkanediyl, $C_5-C_6$-alkenediyl or $C_6$-alkanedienediyl, each of which is unsubstituted or substituted by $C_1-C_5$-alkyl, $C_1-C_5$-alkoxy, fluorine, chlorine or bromine, and in which zero or one methylene group is replaced by oxygen or sulphur, G represents hydrogen (a) or one of the groups (b)

(c)

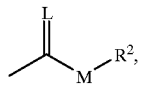

(d)

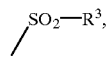

(e)

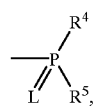

(f)

E or (g)

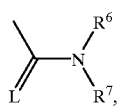

wherein

E represents a metal ion equivalent or an ammonium ion,

L represents oxygen or sulphur and

M represents oxygen or sulphur, $R^1$ represents $C_1-C_{16}$-alkyl, $C_2-C_{16}$-alkenyl, $C_1-C_6$-alkoxy-$C_1-C_6$-alkyl, $C_1-C_6$-alkylthio-$C_1-C_6$-alkyl or poly-$C_1-C_6$-alkoxy-$C_1-C_6$-alkyl, each of which is unsubstituted or substituted by fluorine or chlorine, or unsubstituted or fluorine-, chlorine-, $C_1-C_5$-alkyl- or $C_1-C_5$-alkoxy-substituted $C_3-C_7$-cycloalkyl in which zero one or two not directly adjacent methylene groups are replaced by oxygen or sulphur, represents unsubstituted or fluorine-, chlorine-, bromine-, cyano-, nitro-, $C_1-C_4$-alkyl-, $C_1-C_4$-alkoxy-, $C_1-C_3$-halogenoalkyl-, $C_1-C_3$-halogenoalkoxy-, $C_1-C_4$-alkylthio- or $C_1-C_4$-alkylsulphonyl-substituted phenyl, represents unsubstituted or fluorine-, chlorine-, bromine-, $C_1-C_4$-alkyl-, $C_1-C_4$-alkoxy-, $C_1-C_3$-halogenoalkyl- or $C_1-C_3$-halogenoalkoxy-substituted phenyl-$C_1-C_4$-alkyl, represents pyrazolyl, thiazolyl, pyridyl, pyrimidyl, furanyl or thienyl, each of which is unsubstituted or substituted by fluorine, chlorine, bromine or $C_1-C_4$-alkyl, represents unsubstituted or fluorine-, chlorine-, bromine- or $C_1-C_4$-alkyl-substituted phenoxy-$C_1-C_5$-alkyl or represents pyridyloxy-$C_1-C_5$-alkyl, pyrimidyloxy-$C_1-C_5$-alkyl or thiazolyoxy-$C_1-C_5$-alkyl, each of which is unsubstituted or substituted by fluorine, chlorine, bromine, amino or $C_1-C_4$-alkyl, $R^2$ represents $C_1-C_{16}$-alkyl, $C_1-C_{16}$-alkenyl, $C_1-C_6$-alkoxy-$C_2-C_6$-alkyl or poly-$C_1-C_6$-alkoxy-$C_2-C_6$-alkyl, each of which is unsubstituted or substituted by fluorine or chlorine, represents unsubstituted or fluorine-, chlorine-, $C_1-C_4$-alkyl- or $C_1-C_4$-alkoxy-substituted $C_3-C_7$-cycloalkyl or represents phenyl or benzyl, each of which is unsubstituted or substituted by fluorine, chlorine, bromine, cyano, nitro, $C_1-C_4$-alkyl, $C_1-C_3$-alkoxy, $C_1-C_3$-halogenoalkyl or $C_1-C_3$-halogenoalkoxy, $R^3$ represents unsubstituted or fluorine- or chlorine-substituted $C_1-C_6$-alkyl or represents phenyl or benzyl, each of which is unsubstituted or substituted by fluorine, chlorine, bromine, $C_1-C_5$-alkyl, $C_1-C_5$- alkoxy, $C_1$–$C_3$-halogenoalkyl, $C_1$–$C_3$-halogenoalkoxy, cyano or nitro, $R^4$ and $R^5$ independently of one another each represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, $C_3$–$C_4$-alkenylthio or $C_3$–$C_6$-cycloalkylthio, each of which is unsubstituted or substituted by fluorine or chlorine, or represents phenyl, phenoxy or phenylthio, each of which is unsubstituted or substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl and $R^6$ and $R^7$ independently of one another each represents hydrogen, represents $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_1$–$C_6$-alkyl, each of which is unsubstituted or substituted by halogen, represents unsubstituted or halogen-, $C_1$–$C_5$-halogenoalkyl-, $C_1$–$C_5$-alkyl- or $C_1$–$C_5$-alkoxy-substituted phenyl, represents unsubstituted or halogen-, $C_1$–$C_5$-alkyl-, $C_1$–$C_5$-halogenoalkyl- or $C_1$–$C_5$-alkoxy-substituted benzyl, or together represent a $C_3$–$C_6$-alkylene radical in which zero or one methylene group is replaced by oxygen or sulphur.

4. A compound of the formula (1) according to claim 1 wherein

X represents fluorine, chlorine, bromine, methyl, ethyl, propyl, iso-propyl, methoxy, ethoxy, propoxy, iso-propoxy, trifluoromethyl, difluoromethoxy, trifluoromethoxy, nitro or cyano, Y represents hydrogen, fluorine, chlorine, bromine, methyl, ethyl, n-propyl, i-propyl, n-butyl, i-butyl, tert-butyl, methoxy, ethoxy, propoxy, iso-propoxy, allyloxy, methallyloxy, trifluoromethyl, difluoromethoxy, trifluoromethoxy, nitro or cyano, Z represents fluorine, chlorine, bromine, methyl, ethyl, n-propyl, i-propyl, n-butyl, i-butyl, tert-butyl, methoxy, ethoxy, propoxy, iso-propoxy, difluoromethoxy, trifluoromethyl, trifluoromethoxy, nitro or cyano, n represents 0, 1, 2 or 3, A represents hydrogen or represents $C_1$–$C_8$-alkyl or $C_1$–$C_6$-alkoxy-$C_1$–$C_4$-alkyl, each of which is unsubstituted or substituted by fluorine or chlorine, unsubstituted or fluorine-, chlorine-, methyl-, ethyl-, iso-propyl-, tert-butyl-, ethoxy- or methoxy-substituted $C_5$–$C_6$-cycloalkyl, or represents phenyl or benzyl, each of which is unsubstituted or substituted by fluorine, chlorine, bromine, methyl, ethyl, iso-propyl, tert-butyl, methoxy, ethoxy, trifluoromethyl, difluoromethoxy, trifluoromethoxy, cyano or nitro, B represents hydrogen or represents $C_1$–$C_8$-alkyl or $C_1$–$C_4$-alkoxy-$C_1$–$C_2$-alkyl, each of which is unsubstituted or substituted by fluorine, or A, B and the linking carbon atom represent saturated or unsaturated $C_5$–$C_6$-cycloalkyl in which zero or one methylene group is replaced by oxygen or sulphur and which is unsubstituted or substituted by methyl, ethyl, isopropyl, tert-butyl, trifluoromethyl, methoxy, ethoxy, fluorine, chlorine or phenyl or A, B and the linking carbon atom represent $C_5$–$C_6$-cycloalkyl or $C_5$–$C_6$-cycloalkenyl in which two substituents together with the linking carbon atoms represent $C_5$–$C_6$-alkanediyl, $C_5$–$C_6$-alkenediyl or $C_6$-alkanedienediyl, G represents hydrogen (a) or represents one of the groups

(b)

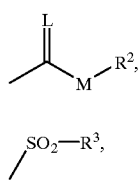

(c)

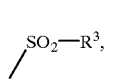

(d)

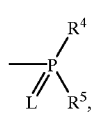

(e)

E or (f)

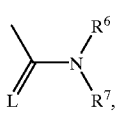

(g)

wherein

E represents a metal ion equivalent or an ammonium ion,

L represents oxygen or sulphur and

M represents oxygen or sulphur, $R^1$ represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl, each of which is unsubstituted or substituted by fluorine or chlorine, or unsubstituted or fluorine-, chlorine-, methyl-, ethyl-, propyl-, i-propyl-, butyl-, i-butyl-, tert-butyl-, methoxy-, ethoxy-, propoxy- or iso-propoxy-substituted $C_3$–$C_6$-cycloalkyl in which zero, one or two not directly adjacent methylene groups are replaced by oxygen or sulphur, represents unsubstituted or fluorine-, chlorine-, bromine-, cyano-, nitro-, methyl-, ethyl-, propyl-, i-propyl-, methoxy-, ethoxy-, trifluoromethyl-, trifluoromethoxy-, methylthio-, ethylthio-, methylsulphonyl- or ethylsulphonyl-substituted phenyl, represents unsubstituted or fluorine-, chlorine-, bromine-, methyl-, ethyl-, propyl-, i-propyl-, methoxy-, ethoxy-, trifluoromethyl- or trifluoromethoxy-substituted benzyl, represents furanyl, thienyl, pyridyl, pyrimidyl, thiazolyl or pyrazolyl, each of which is unsubstituted or substituted by fluorine, chlorine, bromine, methyl or ethyl, represents unsubstituted or fluorine-, chlorine-, methyl- or ethyl-substituted phenoxy-$C_1$–$C_4$-alkyl or represents pyridyloxy-$C_1$–$C_4$-alkyl, pyrimidyloxy-$C_1$–$C_4$-alkyl or thiazolyloxy-$C_1$–$C_4$-alkyl, each of which is unsubstituted or substituted by fluorine, chlorine, amino, methyl or ethyl, $R^2$ represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is unsubstituted or substituted by fluorine or chlorine, represents unsubstituted or fluorine-, chlorine-, methyl-, ethyl-, propyl-, iso-propyl or methoxy-substituted $C_3$–$C_6$-cycloalkyl, or represents phenyl or benzyl, each of which is unsubstituted or substituted by fluorine, chlorine, cyano, nitro, methyl, ethyl, propyl, i-propyl, methoxy, ethoxy, trifluoromethyl or trifluormethoxy, $R^3$ represents methyl, ethyl, propyl, isopropyl, each of which is unsubstituted or substituted by fluorine or chlorine, or represents phenyl or benzyl, each of which is unsubstituted or substituted by fluorine, chlorine, bromine, methyl, ethyl, propyl, iso-propyl, tert-butyl, methoxy, ethoxy, isopropoxy, tert-butoxy, trifluoromethyl, trifluoromethoxy, cyano or nitro, $R^4$ and $R^5$ independently of one another each represents $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio, each of which is unsubstituted or substituted by fluorine or chlorine, or represents phenyl, phenoxy or phenylthio, each of which is unsubstituted or substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio or $C_1$–$C_3$-alkyl and $R^6$ and $R^7$ independently of one another each represents hydrogen, represents $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_1$–$C_4$-alkyl, each of which is unsubstituted or substituted by fluorine or chlorine, represents unsubstituted or fluorine-, chlorine-, bromine-, $C_1$–$C_4$-halogenoalkyl-, $C_1$–$C_4$-alkyl- or $C_1$–$C_4$-alkoxy-substituted phenyl, represents unsubstituted or fluorine-, chlorine-, bromine-, $C_1$–$C_4$-alkyl-, $C_1$–$C_4$-halogenoalkyl- or $C_1$–$C_4$-alkoxy-substituted benzyl, or together represent a $C_1$–$C_6$-alkylene radical in which zero or one methylene group is replaced by oxygen or sulphur.

5. A process for preparing a compound of the formula (1) according to claim 1, comprising the steps of:

(A) intramolecularly condensing a N-acylamino acid ester of the formula (II)

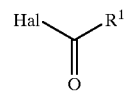

(II)

wherein
A, B, X, Y, Z and n are each as defined in claim 1 and
$R^8$ represents alkyl in the presence of a diluent and in the presence of a base;
producing a compound of the formula (Ia)

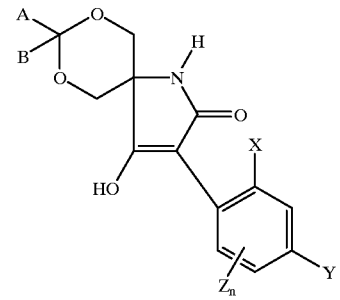

(I-a)

wherein
A, B, X, Y, Z and n are each as defined above
and subsequently reacting the compound of the formula (I-a)

(B)α) with an acyl halide of the formula (III)

(III)

wherein
$R^1$ is as defined in claim 1 and
Hal represents halogen or

α) with a carboxylic anhydride of the formula (IV)

$R^1$—CO—O—CO—$R^1$ (IV)

wherein
$R^1$ is as defined above, or (C) with a chloroformic ester or a chloroformic thiol ester of the formula (V)

$R^2$—M—CO—Cl (V)

wherein
$R^2$ and M are each as defined in claim 1, or (D) with a chloromonothioformic ester or a chlorodithioformic ester of the formula (VI)

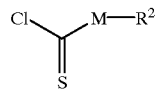

(VI)

wherein
M and $R^2$ are each as defined in claim 1, or (E) with a sulphonyl chloride of the formula (VII)

$R^3$—$SO_2$—Cl (VII)

wherein
R³ is as defined in claim 1, or
(F) with a phosphorus compound of the formula (VIII)

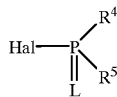
(VIII)

wherein
L, R⁴ and R⁵ are each as defined in claim 1 and
Hal represents halogen, or
(G) with a metal compound or an amine of the formulae (IX) or (X)

Me(OR¹⁰)ₜ  or (IX)

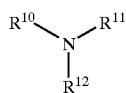
(X)

wherein
Me represents a mono- or divalent metal,
t represents the number 1 or 2 and
R¹⁰, R¹¹, R¹² independently of one another each represents hydrogen or alkyl, or
(H) with a carbamoyl chloride or a thiocarbamoyl chloride of the formula (XI),

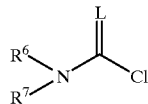
(XI)

wherein
L, R⁶ and R⁷ are each as defined in claim 1.

6. The process of claim 5 wherein the reaction in step (A) is carried out in the presence of a diluent and a base.

7. The process of claim 5 wherein the reaction in steps (B)β), C. D, E, F, and H are carried out in the presence of a diluent and an acid binder.

8. The process of claim 5 wherein the reaction in step G is carried out in the presence of a diluent.

9. A compound of the formula (XII)

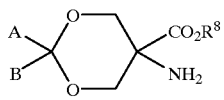
(XII)

wherein
A and B are each as defined in claim 1 and
R⁸ represents alkyl.

10. A compound of the formula (XV)

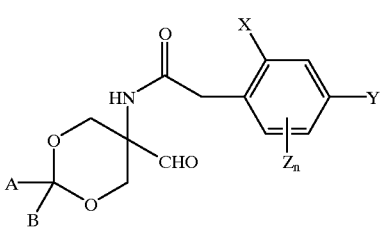
(XV)

wherein
A, B, X, Y, Z and n are each as defined in claim 1.

11. A compound of the formula (XVI)

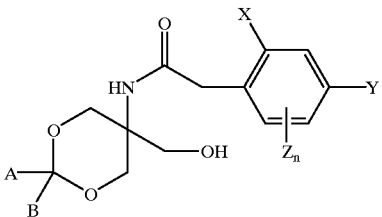
(XVI)

wherein
A, B, X, Y, Z and n are each as defined in claim 1.

12. A pesticide or a herbicide, comprising at least one compound of the formula (I) according to claim 1 and one or more extenders and/or surfactants.

13. A method for controlling pests and undesirable vegetation, comprising the step of allowing a compound of the formula (I) according to claim 1 to act on pests, undesirable vegetation and/or their habitat.

14. A process for preparing a pesticide or a herbicide, comprising the step of mixing a compound of the formula (I) according to claim 1 with extenders and/or surfactants.

15. A process for preparing a compound of the formula (I) according to claim 1,

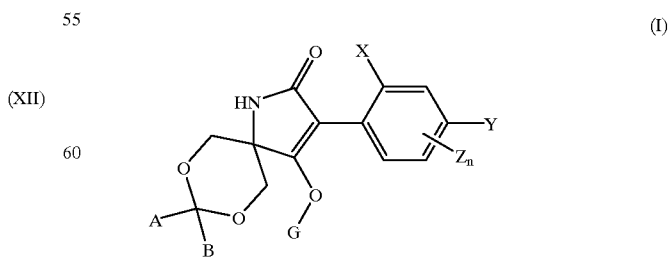
(I)

wherein
A, B, X, Y, Z and n are each as defined in claim 1, and G represents hydrogen,
comprising the step of intramolecularly condensing a N-acylamino acid ester of the formula (II)
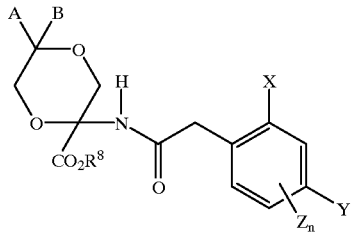
(II)
wherein
A, B, X, Y, Z and n are each as defined in claim 1, and $R^8$ represents alkyl,
producing a compound of the formula (Ia)
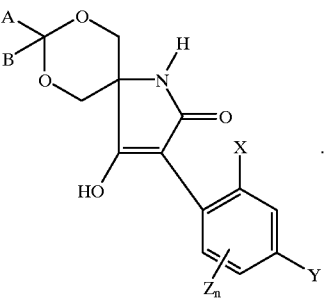
(I-a)
* * * * *